United States Patent
Fagundes et al.

(10) Patent No.: US 10,398,416 B2
(45) Date of Patent: Sep. 3, 2019

(54) BONE MARROW LESION DRILL

(71) Applicant: Smith & Nephew, Inc., Memphis, TN (US)

(72) Inventors: Frederick L. Fagundes, Rehoboth, MA (US); Lily Jeng, St. Louis, MO (US)

(73) Assignee: Smith & Nephew, Inc., Memphis, TN (US)

( * ) Notice: Subject to any disclaimer, the term of this patent is extended or adjusted under 35 U.S.C. 154(b) by 362 days.

(21) Appl. No.: 15/514,872

(22) PCT Filed: Sep. 28, 2015

(86) PCT No.: PCT/US2015/052577
§ 371 (c)(1),
(2) Date: Mar. 28, 2017

(87) PCT Pub. No.: WO2016/053834
PCT Pub. Date: Apr. 7, 2016

(65) Prior Publication Data
US 2017/0209129 A1     Jul. 27, 2017

Related U.S. Application Data

(60) Provisional application No. 62/058,586, filed on Oct. 1, 2014.

(51) Int. Cl.
*A61B 17/00* (2006.01)
*A61B 10/02* (2006.01)
(Continued)

(52) U.S. Cl.
CPC ............ *A61B 10/025* (2013.01); *A61B 10/02* (2013.01); *A61B 17/34* (2013.01);
(Continued)

(58) Field of Classification Search
None
See application file for complete search history.

(56) References Cited

U.S. PATENT DOCUMENTS

| | | | |
|---|---|---|---|
| 5,036,695 | A | 8/1991 | Bergeron |
| 5,591,170 | A | 1/1997 | Spievack |

(Continued)

FOREIGN PATENT DOCUMENTS

| | | | |
|---|---|---|---|
| EP | 1421907 A1 | 5/2004 | |
| EP | 1785103 A1 | 5/2007 | |

(Continued)

OTHER PUBLICATIONS

JP OA for App No. 2015-545818 dated Aug. 18, 2017, 7 pages.
(Continued)

*Primary Examiner* — Sameh R Boles
(74) *Attorney, Agent, or Firm* — Burns & Levinson, LLP; Joseph M. Maraia

(57) ABSTRACT

Devices, systems, methods, and kits are provided for accessing and treating bone marrow lesions in intraosseous spaces of bones by reversibly coupling a drill, including a surgical power drill, to a stylet reversibly inserted within and coupled with a cannula to provide for concurrent or synchronized rotation of the stylet and the cannula when drilling into a bone. Also provided are devices, systems, methods, and kits for their use for uncoupling a stylet from a cannula once the cannula is in a desired position in a bone, removal of the stylet to provide an open lumen to the desired location in the bone, and reversible attachment of an access device to the proximal end of the cannula to deliver and/or withdraw a substance (such as bone graft substitute) from the accessed lesion. Still further are provided devices, systems, methods, and kits for subsequently removing the lumen from the bone, including by reinserting the stylet into the lumen, recoupling (Continued)

the stylet with the lumen, and back drilling, including by power drill, the two components out of the bone.

21 Claims, 15 Drawing Sheets

(51) Int. Cl.
  *A61B 17/34* (2006.01)
  *A61B 90/00* (2016.01)
(52) U.S. Cl.
  CPC ...... *A61B 17/3472* (2013.01); *A61B 17/3494* (2013.01); *A61B 90/03* (2016.02); *A61B 2010/0258* (2013.01)

(56) References Cited

U.S. PATENT DOCUMENTS

| | | | |
|---|---|---|---|
| 5,817,095 | A | 10/1998 | Smith |
| 6,221,029 | B1 * | 4/2001 | Mathis ............... A61B 10/0233 600/564 |
| 2002/0032447 | A1 | 3/2002 | Weikel |
| 2004/0199166 | A1 | 10/2004 | Schmieding |
| 2004/0208717 | A1 | 10/2004 | Greenhalgh |
| 2005/0240193 | A1 | 10/2005 | Reiley |
| 2007/0123921 | A1 | 5/2007 | Ek |
| 2008/0045857 | A1 | 2/2008 | Miller et al. |
| 2008/0114364 | A1 | 5/2008 | Schumacher |
| 2008/0221505 | A1 | 9/2008 | Betts |
| 2009/0228013 | A1 | 9/2009 | Ferragamo |
| 2010/0168750 | A1 | 7/2010 | Sherman |
| 2011/0190832 | A1 | 8/2011 | Brenzel |
| 2012/0271357 | A1 | 10/2012 | Kadri |
| 2013/0184610 | A1 | 7/2013 | Bourque |
| 2013/0261650 | A1 | 10/2013 | Hanson et al. |

FOREIGN PATENT DOCUMENTS

| | | |
|---|---|---|
| EP | 2098177 A1 | 9/2009 |
| JP | 2005152650 A2 | 6/2005 |
| JP | 4801225 B1 | 10/2011 |
| WO | 2006060420 A1 | 6/2006 |
| WO | 2012125546 A1 | 9/2012 |
| WO | 2013138482 A2 | 9/2013 |

OTHER PUBLICATIONS

EP OA for App No. 13735099.7 dated Aug. 4, 2017, 6 pages.
EP OA for App No. 13811705.6 dated Jul. 11, 2017, 4 pages.
International Preliminary Report on Patentability from related PCT Application No. PCT/US2015/052577 dated Apr. 4, 2017.

* cited by examiner

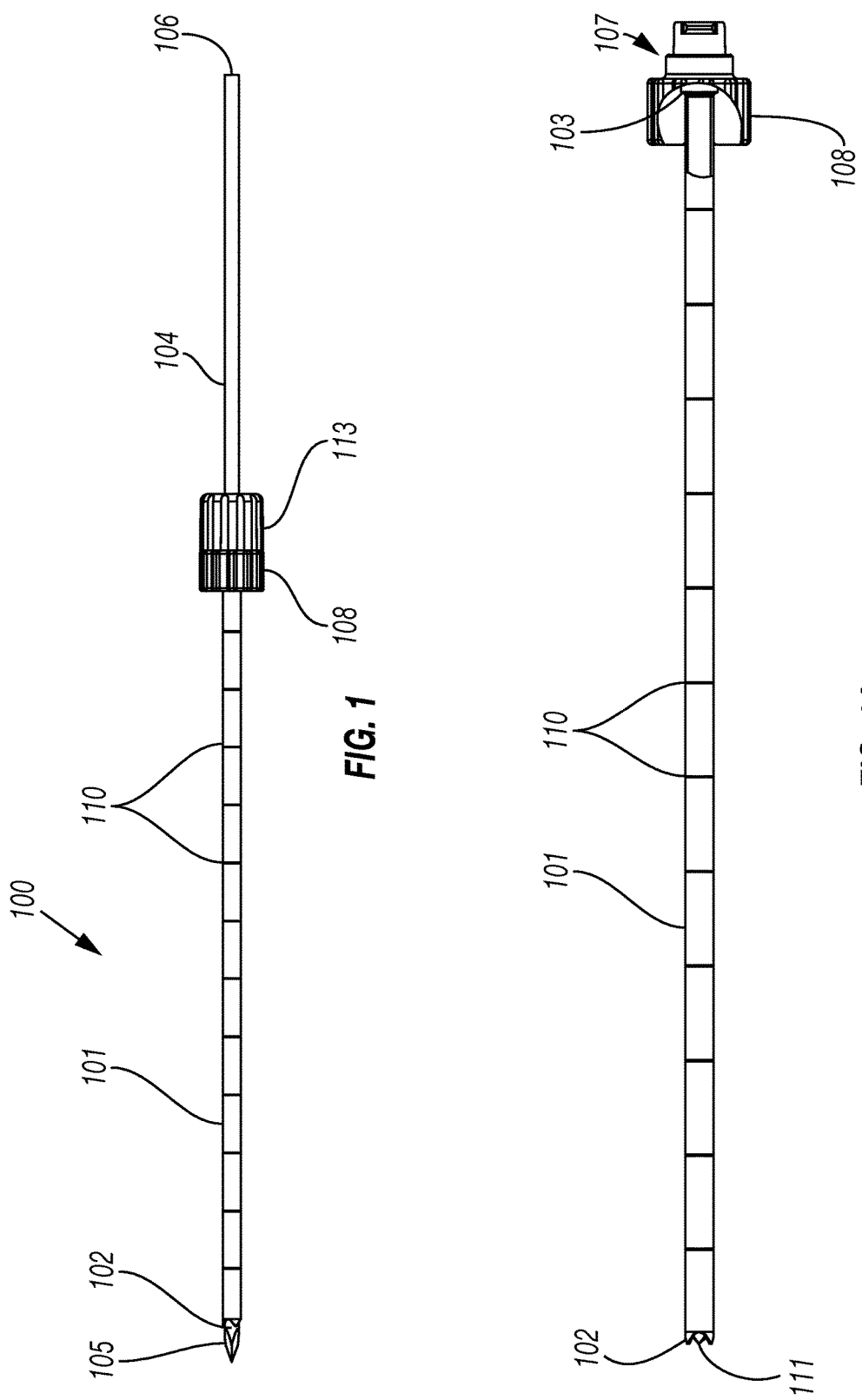

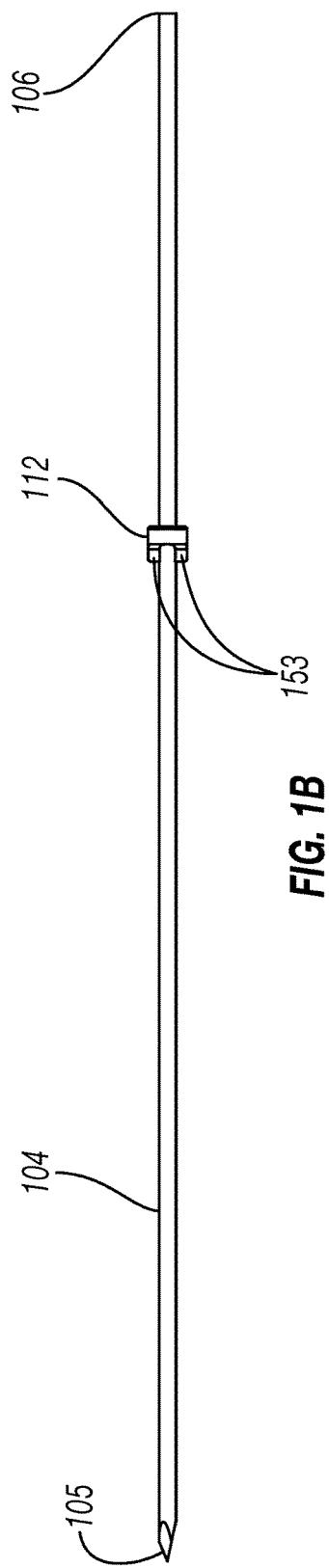

FIG. 3B
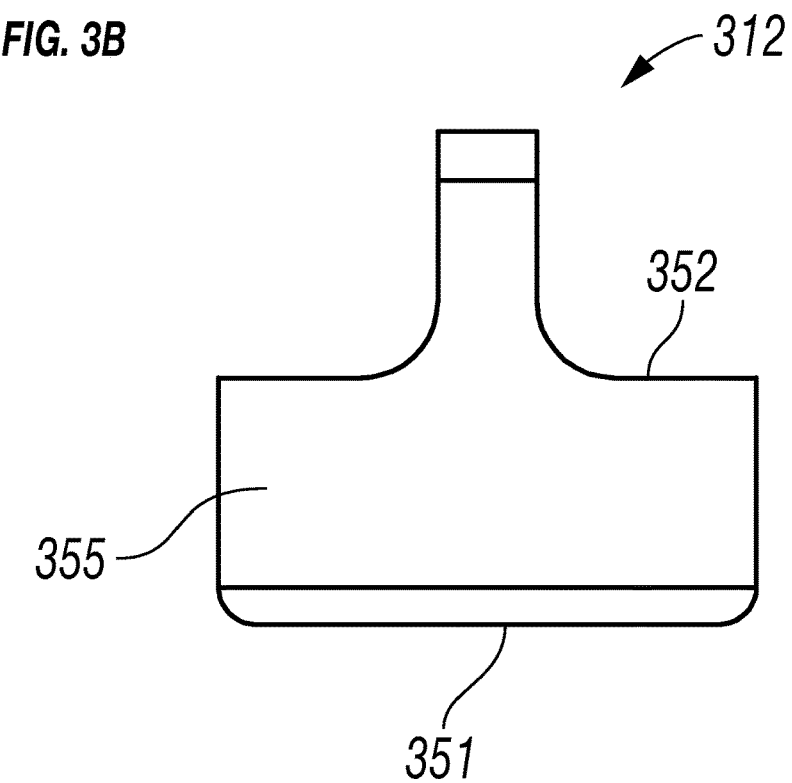
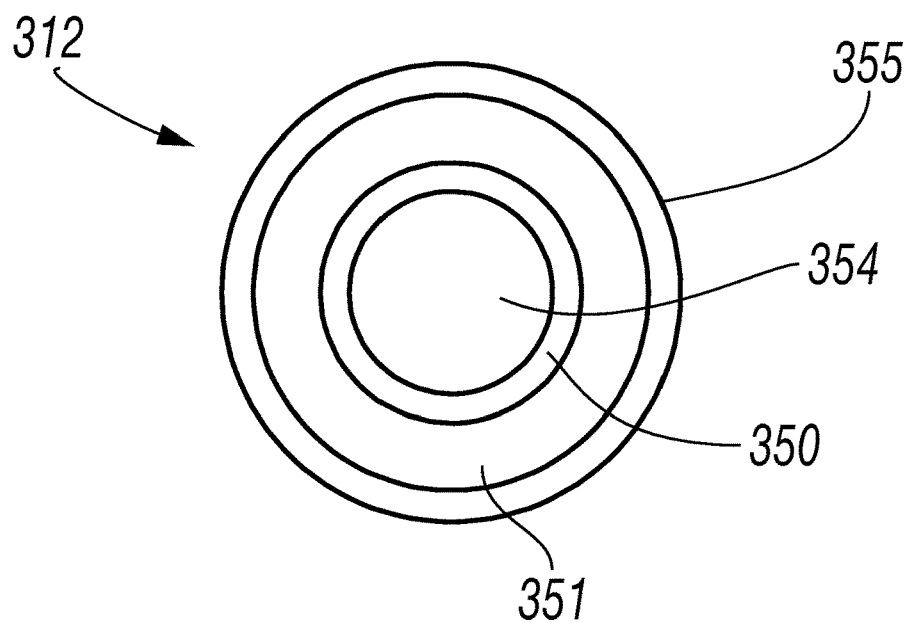
FIG. 3C

BONE MARROW LESION DRILL

CROSS-REFERENCE TO RELATED APPLICATIONS

This application is the U.S. National Stage of International Application No. PCT/US2015/052577, filed on Sep. 28, 2015, which claims the benefit of U.S. Provisional Application No. 62/058,586 filed on Oct. 1, 2014, the entire contents of the above-identified applications are incorporated herein by reference in their entirety.

BACKGROUND

The present disclosure relates to instruments for accessing intraosseous regions of bone for conveying thereto agents such as bone graft substitutes. For example, disclosed and described are instruments, systems, kits, and methods for accessing intraosseous regions of bone (bone marrow containing regions of bone), including, for example, in accessing intraosseous spaces at, near, or within a bone marrow lesion ("BML"). Thus, one aspect of this invention relates to treating BMLs by using the disclosed instruments and methods to access regions of bone pertinent to a BML to be treated and providing a conveyance for a treatment substance, such as a bone graft substitute ("BGS"), to be injected into a region of bone at, near, or within by a BML. In a non-limiting example, embodiments of the devices, systems, kits, and methods may be used for bone augmentation in the knee.

More particularly, for example, the instruments, systems, kits, and methods disclosed may include an elongated tubular member (a cannula, a cannula needle, or a cannulated probe) having distal and proximal ends, an elongated wire (a stylet) having distal and proximal ends, the distal end which may be sharpened and/or pointed, the elongated wire slidably disposable within at least one lumen of the cannula, a drill stop having distal and proximal ends and attachable to the stylet, the drill stop also having drill stop extensions extending distally from the distal end and coaxially with the axis of the lumen and stylet, a luer lock (or "luer-type lock," used interchangeably herein with the term "luer lock" when referring to the invention disclosed herein) having distal and proximal ends and a body through which runs a channel between the proximal and distal ends, the luer-type lock attachable to the proximal end of the cannula, the luer lock body having luer lock (luer-type lock) slots extending distally into the luer lock from the proximal end of the luer lock and coaxially with the axis of the cannula. Further, the drill stop extensions are slidably but reversibly engageable within the luer-type lock slots when the distal end of the drill stop, from which the drill stop extensions extend, is proximate proximal end of the luer-type lock, in which the luer lock slots are located. Because the drill stop, and thus the drill stop extensions, are attachable to the stylet, and the luer lock and the luer lock slots are attachable to the cannula, when attached, rotation about the axis of the stylet only causes concurrent or synchronized rotation about the cannula (and vice versa).

The luer-type lock may further have luer lock projections (luer-type lock projections) that extend perpendicularly (or radially about the width of the projections) from the proximal end of the luer lock.

The coupling of the cannula and the stylet (via reversibly insertion of the drill stop extensions within the luer-type lock slots) may be further reversibly coupled by a luer-type lock cap (cap) having proximal and distal ends where the cap is slidably engageable over the proximal end of the stylet through a stylet opening in the proximal end of the cap where the internal diameter of the stylet opening is greater than the exterior diameter of the stylet, yet is less than the external diameter of the drill stop and the external diameter of at least a region proximate the proximal end of the luer lock containing the luer lock projections.

The distal end of the cap has a distal opening to and an internal threaded chamber of the cap. The internal diameters of the distal opening and internal threaded chamber of the cap are greater than the external diameters of the drill stop and at least a region proximate the proximal end of the luer lock containing the luer lock projections. Therefore, when the distal end of the drill stop is proximate the proximal end of the luer-type lock, the cap receives and retains the entire drill stop and at least a region proximate the proximal end of the luer-type lock containing the luer lock projections. The internal threads of the luer-type lock cap are then threadably engageable over the luer lock projections and the cap reversibly tightened against the proximal end of the luer lock, including reversibly coupling the drill stop on the stylet with the luer lock on the cannula by reversibly holding together the drill stop extensions within the luer lock slots.

The assembled devices, systems, and kits are further reversibly or permanently connectable with drill, such as a manual drill, a power drill (e.g., a power surgical drill), and a wire drill. The drills may drill in one direction or be reversible drills. In any event, the drill is capable of engaging the proximal end or end region of the stylet (elongated wire) of the device and of thereby rotating the entire assembled tool, at set or variable speeds and/or directions controlled by an operator, a computer algorithm, or both. A drill may be connected to the device, such as to the proximal end of the stylet, throughout the assembly, use, and disassembly of the device or at any times therein, provided it is coupled to the device when drilling is needed.

In embodiments where a drill connects to and rotates the elongated wire (stylet) portion of the device, the elongated wire may be reversibly coupled to the cannula, as discussed above and in detail below, rotation about the axis of the stylet causes concurrent or synchronized rotation about the axis of the cannula. Such concurrent or synchronized rotation assists in inserting both the cannula and stylet into a desired location within an intraosseous space of a bone; it also assists in drilling into the surface of bone. For example, in some embodiments, the distal (drilling) end of the cannula may have teeth, and/or the tip of the stylet may extend beyond the end of the cannula (as discussed below) and be pointed and/or sharpened, such that pointed and/or sharpened tip of the stylet makes the first entry point of the device into bone (in effect establishing an initial "pilot hole" in the surface of the bone from which drilling may begin). Without limitation, or bound by theory, this process of initiating drilling into bone may, among other things, help hold and stabilize the device at an initial desired location on the surface of a bone to be drilled by the tip of the stylet forming a type of "pilot hole," thereby helping to alleviate problems known in the art such as sliding and skipping of a bone access device on a bone's surface (which may be dense and/or slippery) when trying to initiate drilling at a desired location on the bone. These features further assist entry of the device into the intraosseous region of a bone when the device is rotated by a drill.

In embodiments, after the cannula—stylet coupled device has been advanced by drilling to a desired location in an intraosseous region, the cannula is kept in place in order to act as a conduit for injection of a desired substance into the accessed bone space (e.g., for the injection of bone graft substitute into a bone marrow lesion accessed by the device). While the cannula remains in place, the cap is unthreaded from the projections of the luer lock, reversibly removing this aspect of coupling the stylet and cannula. The stylet is then reversibly removed from the cannula, and therefore simultaneously the extensions of the drill slot are reversibly disengaged from within the slots of the luer lock.

When the elongated wire has been fully removed from the cannula, an injection device, such as by non-limiting example a syringe, may be reversibly attached to the luer lock at the proximal end of the cannula and a desired substance (such as BGS) may be injected into an accessed intraosseous space, such as one having a BML. Following injection, the cannula may be removed from the bone, for example, by manual force (with or without the injection device (e.g., a syringe) attached to the luer lock), such as by a surgeon removing the cannula by manually pulling and/or twisting.

As discussed below, in certain embodiments of the invention, after injecting a desired amount of treatment substance (e.g., BGS) into a BML, the lumen may be removed from the bone with, for example, the assistance of a drill. In these embodiments, the injection device is removed from the distal end of the cannula following use of the injection device, and the stylet is then reinserted (or inserted if a new or different stylet is used from the original elongated wire) into the cannula (where the reinserted stylet can include the same cannula first used in drilling, which may have the same or opposite locations of sharpened ends relative the ends of the cannula, or, for example, may be a dual blunt end stylet). Next, the device is fully reassembled including, for example, reassembling the luer lock—drill stop coupling and reattaching the cap to the luer-lock. In such a reassembled device (or any similar reassembly that reconnects a stylet with the cannula) the proximal end and/or region of the stylet may be used to assist in removing the device from the bone. For example, a manual or power surgical drill may be attached to the proximal end and/or region of the stylet and the drill used to rotate the stylet about its axis causing concurrent or synchronized rotation about the cannula which assists in backing the device out of the bone.

In other embodiments of the invention, a device that is capable of withdrawing (e.g., applying a suction force, e.g., a syringe, a collection device, a vacuum device, and the like) is also reversibly attachable to the luer lock at the proximal region of the cannula end after the stylet has been withdrawn. In embodiments, when a withdrawing device is used, it is coupled to the luer lock at the proximal region of the cannula end and used to withdraw a sample from the accessed intraosseous space (such as a BML). In embodiments where a withdrawing device is used, it is reversibly attached to the luer lock and the proximal end of the lumen (generally but not necessarily after the stylet has been removed) and used to apply a suction force to an accessed region and capture any sample therefrom before being disengaged from the luer lock and cannula. In such embodiments, following disengagement of the withdrawal device from the luer lock and cannula, an injection device is then reversibly attached to the luer lock at the proximal region of the cannula end of the cannula and a desired substance (such as BGS) may be injected into an accessed intraosseous space, such as one having a BML. However, it is within the scope of this invention to use the described devices only to withdraw a sample from an intraosseous space. In such cases, for example, the drilling into the intraosseous space, uncoupling the stylet (and removing it from) the cannula (and disengaging related components) are the same as for other uses herein, the difference being that after disengaging the withdrawal device the cannula would be removed without an injection step (or injection device) (such as by reassembling the device including reinserting a stylet and using rotation of the stylet to back the cannula out of the bone).

As discussed above, the device may also be reassembled, for example, by removing the substance injection device (e.g. syringe) from the proximal end of the luer lock, and reinserting the stylet into a lumen of the cannula, reinserting the drill stop extensions of the drill stop (attached to the stylet) into the luer lock slots (the luer lock slots part of the luer lock which is attached to the cannula) and assuring stable recoupling the stylet and cannula by rethreading the luer lock cap over the drill stop and over at least a region proximate the proximal end of the luer lock containing the luer lock projections, wherein inner threads of the cap threadably engage over the luer lock projections. Once reassembled (recoupled) the drill may be reattached to or near the proximal end of the stylet (if it was removed during any preceding aspect, which is not necessarily required), and the drill activated in the opposite direction from drilling in order to back the cannula and stylet out of the accessed bone.

There are currently available manual devices that are able to couple a stylet and a cannulated needle and access intraosseous sites. These devices, such as Jamshidi® or T-handle needles, also allow for the ability to couple a syringe to the device to deliver substances, including bone marrow, bone marrow substitutes, and bone graft substitutes, into an accessed intraosseous space.

However, the BML access instruments, systems, and kits known in the art are solely to manual drive for twisting the instrument on insertion and removal—not to power drive. Manual drives of intraosseous region (e.g., BML) access and treatment instruments complicate accessing a desired intraosseous region for several reasons. For non-limiting examples, the outside of bone is dense, hard, and slippery, while breaching the outside of bone at a precise location is important in order to access a desired intraosseous location with precision. A medical professional must apply a sufficient amount of pressure and rotation to an access device to both begin insertion accurately at the desired location on the outside surface of the bone, and to reach a desired location within a bone; too much pressure may damage the bone and lack of sufficient pressure and speed of rotation may cause the instrument to slip (skid, or jump) from its desired insertion location on the surface of the bone. Additionally, lack of sufficient pressure and speed of rotation may adversely affect a surgeon's control over the course of a tunnel within a bone, making it, for example, possible to stop short of, overshoot, or otherwise miss accessing desired BML locations, and even to drill completely through a bone, such as back out of an opposing side of a bone such as a femur. Lack of powered drilling may also make the insertion, and removal, of bone access devices more physically demanding, placing additional burden on a surgeon, and raising the possibility of damaging, for example, a surgeon's hand and/or wrist. Easing the difficulties associated with manually inserting tools may also allow surgeons so more readily focus on the precision of the placement, advancement and final position of the tool.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

The present disclosure relates to instruments and methods for their use for accessing internal regions of bone, such as intraosseous regions of bone (bone marrow containing regions) for conveying thereto agents such as bone graft substitutes, and/or for removing samples therefrom. For example, embodiments of the invention relate to instruments, systems, kits, and methods for accessing intraosseous regions of bone, including for example for accessing intraosseous spaces at, near, or within a bone marrow lesion ("BML"), for example in the augmentation of bone in or near the lesion. Thus, embodiments of this invention relate to treating BML by using the disclosed instruments and methods to access regions of bone pertinent to a BML to be treated, providing a conveyance for a BML treatment substance such as a bone graft substitute ("BGS") to be injected into a region of bone at, near, or within by a BML. In a non-limiting example, embodiments of the devices, systems, kits, and methods may be used for bone augmentation in the knee.

The instruments, systems, kits, and methods disclosed may include in certain embodiments an elongated tubular member (e.g., a cannula, a cannula needle, or a cannulated probe) having proximal and distal ends, an elongated wire (e.g., a stylet) having proximal and distal ends, where the distal end may be sharpened and/or pointed, the elongated wire slidably disposable within a lumen of the elongated tubular member.

Further, embodiments of the invention may include a drill stop having distal and proximal ends and attachable to the elongated wire (stylet), the drill stop also having drill stop extensions extending distally from the distal end and coaxially with the axis of the lumen and stylet. Further provided in embodiments is a luer lock (luer-type lock) having distal and proximal ends and a body through which runs a channel between the proximal and distal ends of the luer lock, the luer-type lock attachable to the proximal end of the cannula, the luer lock body having luer lock slots extending distally into the luer lock from the proximal end of the luer lock and coaxially with the axis of the cannula. The luer lock also has luer lock projections which project radially from at or near the proximal end of the luer lock.

In embodiments, the drill stop extensions are slidably but reversibly engageable within the luer lock slots when the distal end of the drill stop, from which the drill stop extensions extend, is at or near the proximal end of the luer lock (i.e., when the stylet is at least partially inserted into the cannula such that the drill stop on the stylet abuts or is close to abutting the proximal end of the luer lock in which the luer lock slots are located). Because the drill stop, and thus the drill stop extensions, are attachable to the stylet, and because the luer lock and the luer lock slots are attachable to the cannula, when attached, reversible coupling of the drill stop extensions within the luer lock slots reversibly couples the elongated wire with the elongated tubular member (and when so coupled, for example, rotation about the axis of the stylet only causes concurrent or synchronized rotation about the cannula (and vice versa)).

The drill stop extensions within the luer lock slots may be further reversibly coupled and held stable by a luer lock cap (cap) having proximal and distal ends where the cap is slidably engageable over the proximal end of the stylet through a stylet opening in the proximal end of the cap where the stylet opening allows the exterior diameter of the stylet to pass through, yet is too small in diameter to allow the drill stop and at least a region at or near the proximal end of the luer lock containing the luer lock projections to pass. However, the distal end of the cap has a distal opening to and an internal threaded chamber of the cap. The internal diameters of the distal opening and internal threaded chamber of the cap are greater than the external diameters of the drill stop and at least a region at or near the proximal end of the luer lock containing the luer lock projections.

Therefore, when the distal end of the drill stop is proximate the proximal end of the luer lock, and the luer lock cap is, for example, slid over the proximal end of the stylet and toward to drill stop and the luer lock, the distal opening and internal threaded chamber of the cap receive and retain the entire drill stop and at least a region near or at the proximal end of the luer lock containing the luer lock projections. The internal threads of the luer lock cap may then be threadably engaged over the luer lock projections and the cap reversibly tightened against the proximal end of the luer lock, including reversibly coupling the drill stop on the stylet with the luer lock on the cannula by reversibly holding together the drill stop extensions within the luer lock slots.

The assembled devices, systems, kits, and methods are further reversibly or permanently connectable with a surgical power drill, such as a power wire drill (e.g., the proximal end of the stylet reversibly attachable to a chuck on the drill) capable of rotating the tool about its axis in order to drill the assembled device into a desired location on and/or into a bone; as discussed briefly above, and in detail below, rotation about the axis of the stylet when coupled with the cannula, causes concurrent or synchronized rotation about the cannula. It is understood, but not by limitation, that power rotation assists at least in fast and accurate placement of the cannula to a desired location in the bone, and reduces physical demands on the surgeon and the instrument.

In embodiments, after the cannula—stylet coupled device has been drilled to a desired intraosseous location the cannula is kept in place in order to act as a conduit for injection of a desired substance into the accessed bone space (e.g., BGS). While the cannula remains in place, the cap is unthreaded from the projections of the luer lock, reversibly removing this aspect of coupling the stylet and cannula. The stylet is then reversibly removed from the cannula, and therefore simultaneously the extensions of the drill slot are reversibly disengaged from within the slots of the luer lock).

When the elongated wire has been fully removed from the cannula, in certain embodiments, a suction device (such as a syringe) may be may be reversibly attached to the luer lock at the proximal end of the cannula and a desired substance (such as necrotic bone tissues) may be withdrawn into the suction device. The suction device may then be detached from the luer lock and cannula.

An injector, such as a syringe, is then reversibly attached to the luer lock at the proximal end of the cannula (in embodiments, for example, when no withdrawing device is used, the injector is attached to the luer lock cannula end directly following removal of the guide wire from the cannula) and a desired substance (such as BGS) may be injected into the accessed intraosseous space, such as a location having a BML. Following injection, the cannula may be removed from the bone, for example, by manual force (with or without the substance injection device attached to the luer lock), such as by a surgeon removing the cannula by manually pulling and/or twisting.

The device may also be reassembled, for example, by removing the substance injection device (e.g. syringe) from the proximal end of the luer lock, and reinserting the stylet into a lumen of the cannula, reinserting the drill stop extensions of the drill stop (attached to the stylet) into the luer lock slots (the luer lock slots part of the luer lock which is attached to the cannula) and assuring stable recoupling the stylet and cannula by rethreading the luer lock cap over the drill stop and over at least a region proximate the proximal end of the luer lock containing the luer lock projections, wherein inner threads of the cap threadably engage over the luer lock projections. Once reassembled (recoupled) the drill may be reattached at or near the proximal end of the stylet (if it was removed during any preceding aspect, which is not necessarily required), and the drill activated (e.g., in the opposite direction from drilling) in order to back the cannula and stylet out of the accessed bone.

Further, in embodiments in which the wire is connectable to a power drill and concurrently rotates both the tubular member and the wire, the tubular member is reversibly coupleable to the wire. For example, in embodiments of the disclosed invention, the wire has a drill stop permanently or firmly attached to it at a location at which when coupled to the proximal end of the cannula, the wire will extend the lumen of the tubular member to a desired location. For example, where it is desired that a distal region of the wire (e.g., a pointed distal portion) should protrude beyond the distal end of the tubular member, the drill stop is attached at a location on the wire to so position the wire when it is coupled to the tubular member.

In more detail, in embodiments, the drill stop is reversibly engageable with a component at the proximal end and opening of the lumen of the tubular member. For example, in embodiments, the drill stop may have positive mating features (prongs) extending substantially parallel with the wire and the tubular member and reversibly engageable with negative mating features (slots) located in a receptive structure at the proximal end of the tubular structure. In embodiments of the invention, the receptive structure may be the luer lock referred to above at the proximal end of the tubular member that has been modified to contain the negative mating features (slots) engageable with the prongs of the drill stop. Such configurations may further be reversibly held together by a and additional component, a luer lock cap (cap) that may be slidable over the distal region of the wire, over the drill stop, and securable over the tubular member, for example, by internal threads in the cap device threadably engageable with external projections (extending substantially perpendicularly or radially from the direction of the axis of the tubular member) from the luer lock at or near the proximal end of the luer lock, which is attachable to the proximal end of the tubular member.

In use, a medical professional couples (or ensures that the coupling has already been made) the wire with the tubular member by inserting the wire into a lumen of the tubular device, engaging the prongs of the drill stop on the wire with the slots of the luer lock at the proximal ends of the luer lock and tubular member, slides the cap over the distal end of the wire, over the drill stop on the wire, and threads it over the projections from the luer lock via internal threads in the cap. This ensures that the wire is firmly, but reversibly, coupled with the tubular member via the threaded cap. Next, a drill is attached at or near the distal end of the wire and the wire is rotated using the power drill.

The rotation by the power drill assists accurate and safe entry of the device into bone, such as into the intraosseous region of a bone, including reducing the force required by a surgeon in drilling the device into a bone.

Once the device has been drilled to a desired depth, the drill may (or may not) be removed from the wire. The wire is then uncoupled from the tubular member simply by unthreading the cap from the projections of the luer lock and pulling the wire from the tubular member (and in doing so, the prongs of the drill stop disengage from the slots of the luer lock). The tubular member then remains in place at the desired location in the bone, allowing the proximal end of the luer lock at the proximal end of the cannula to be reversibly coupled with a source (e.g., a syringe) of BML treatment substance to be injected to intraosseous area accessed by the cannula.

In some non-limiting embodiments, the invention also provides for reversibly coupling of the luer lock proximal end of the cannula with a source of suction for removing (for example) samples of the accessed bone material, such as necrotic bone tissue. In some such embodiments, the source of suction may be reversibly coupled to the luer lock and cannula before the injection source is coupled thereto. In such cases, the suction source is coupled to the luer lock and cannula, used and subsequently uncoupled from the luer lock and cannula before the injection source is reversibly coupled to the luer lock and cannula (although the order of attachments of the injection and suction sources to the luer lock and proximal end of the cannula may vary and be within the scope of this invention).

When this is completed, the tubular member may be removed manually by a medical professional twisting and/or pulling the tubular member from the bone. A drill may also be used to reverse out the tubular member to assure accurate and precise withdrawal and minimal damage to surrounding bone tissue. To do so, for example, a medical professional recouples the device essentially as described above. For example, one reinserts the stylet into the lumen of the tubular member, couples the reinserted wire to the tubular member by reinserting the prongs (or extensions) of the drill stop into the slots on the luer lock of the proximal end of the tubular member, and reapplies the cap by threading it over the drill stop and the an area at or near the proximal end of the luer lock having the luer lock projections. The cap is then tightened against the luer lock to ensure close coupling of the cannula (via the luer lock projections and slots) and the stylet (via the drill stop, cap, and drill stop extensions). The drill is then reattached (if necessary) at or near the proximal end of the elongated wire and operated in a reverse direction to that of insertion, in order to reverse rotate both the tubular member and the wire from the bone.

In some non-limiting embodiments, the invention relates to a medical device for accessing intraosseous space including an elongated tubular member having a proximal end and a distal end; at least one lumen extending through the elongated tubular member having a proximal opening and a distal opening; a luer lock having a proximal end, a distal end, an internal channel extending through the luer lock between the proximal end and the distal end, and permanently attachable to the proximal end of the elongated tubular member; the luer lock further having an external wall with at least two slots therein extending from the proximal end of the luer lock toward the distal end of the luer lock coaxially with the internal channel of the luer lock; the luer lock still further containing at least two luer lock projections projecting radially from the luer lock wall proximate the luer lock proximal end; the medical instrument further containing an elongated wire having a proximal end and a distal end, the elongated wire slidably engageable within the lumen of the elongated tubular member; a drill stop with a distal end, a proximal end, and a channel within the drill stop extending between the proximal end and the distal end, the drill stop channel slidably engageable over the elongated wire, and permanently attachable to the elongated wire; the drill stop further having at least two drill stop extensions extending distally from the distal end of the drill stop and coaxially with the drill stop channel, the drill stop extensions reversibly insertable within the slots of the luer lock when the distal end of the drill stop is at or near the proximal end of the luer lock; and the medical device also having a luer lock cap with a proximal end, a distal end, a proximal end wall having at least one elongated wire opening therein, the elongated wire opening slidably receivable of the elongated wire, an internal threaded chamber and a distal opening of the internal threaded chamber at the distal end of the luer lock cap, the internal threaded chamber reversibly receivable of the drill stop and at least a proximal portion of the luer lock including the luer lock projections and reversibly threadable over the projections of the luer lock to reversibly hold the distal end of the drill stop against the proximal end of the luer lock, the extensions of the drill stop in the slots of the luer lock, and the elongated wire within the elongated tubular member.

Additional embodiments include, for example, the above-described medical device further having a luer lock handle, wherein the handle may have external gripping features on an exterior.

Further embodiments of the invention include the above-described medical devices further having a proximal exterior region of the luer lock at and near the proximal end of the luer lock, and a luer lock handle distal to the proximal exterior region, the external diameter of the proximal exterior region being less than the external diameter of the luer lock handle.

Additionally, certain embodiments of the invention relate to certain of the above-described medical devices having external gripping features on an exterior of the luer lock handle.

In additional embodiments of the invention, certain above-described medical devices may further have a luer lock handle located immediately distal to the proximal exterior region of a luer lock.

Additionally, in aspects of the invention disclosed herein, the distal end of the elongated wire is pointed. Also, there may be teeth in the distal end of the elongated tubular member.

Other aspects of the invention relate to certain of the embodiments and combinations of embodiments described herein wherein the drill stop of the device is attachable to a location on the elongated wire to allow a desired amount of wire distal the drill stop to slidably enter the proximal end of the luer lock and the elongated tubular member and extend distally beyond the distal end of the elongated tubular member.

In embodiments of the invention, a drill is attachable to the proximal end of the elongated wire, wherein the drill may be a power surgical drill capable of rotating the elongated wire about the axis of the wire. In such or related embodiments, rotation of the elongated wire causes rotation of the elongated tubular member when coupled to the elongated wire.

In other non-limiting embodiments of the invention disclosed herein, the disclosure relates to a method of accessing an intraosseous region of a bone and injecting a desired composition therein wherein the method involves assembling the medical instruments discussed above; attaching a drill to the proximal end of the elongated wire of the assembled instrument; accessing the surface of a bone to be drilled into at a desired location to drill to reach a desired intraosseous space; placing a distal end of the assembled device at the desired location on the surface of the bone to be drilled into; drilling into the bone by rotating the elongated wire and the coupled elongated tubular member to a desired location and depth in the bone to access the desired bone lesion; maintaining the elongated tubular member in the bone at the desired location and depth within the bone to access the desired bone lesion; unthreading the internal threads of the luer lock cap from the projections of the luer lock; withdrawing elongated wire from the at least one lumen of the elongated tubular member and the drill stop extensions from within the luer lock slots; reversibly attaching to the proximal end of the luer lock a delivery device for delivering a substance to be delivered into the desired intraosseous location; delivering a desired amount of the substance into the proximal opening of the luer lock, through the lumen of the elongated tubular member, and exiting the distal opening of the elongated tubular member into the desired intraosseous space; and removing the elongated tubular member from the bone.

Additional embodiments of the invention include, for example, the above-described method further involving disengaging the delivery device from the proximal end of the luer lock after injecting the desired substance into the intraosseous space; reinserting the elongated wire into the channel of the luer lock and through the lumen of the elongated tubular member; reinserting the extensions of the drill stop into the slots of the luer lock; rethreading the luer lock cap over the projections of the luer lock to threadably engage the luer lock projections with the internal threads of the luer lock cap; using the drill in the direction opposite the drilling direction to rotate the elongated wire about its axis and the coupled elongated tubular member about its axis; and backing the reassembled device out of the bone.

Additionally, embodiments of the above two paragraphs, for example, may further involve manually removing the elongated tubular member from the bone, as well as the use (in drilling and/or removal) of a manual drill, or a wire or surgical power drill.

Still further, the above methods may also involve in some embodiments the elongated wire of the assembled device extending distally beyond the distal end of the elongated tubular member, assisting in guiding the device into the desired location in the bone, as well as in gaining an initial stable point of contact of the needle and cannula on and in the outer layer of the bone (the cortex of bone can be slippery making precise initiating of drilling difficult as a drill tip tends to slip and slide on the surface, whereas it is believed that a sharpened pointed tip may help to address this issue by quickly gaining an initial pilot hole). Similarly, in embodiments of the invention, the cannula (or elongated tubular member) may have teeth about the circumference of its distal opening. While not being bound by theory, it is understood that these teeth may assist especially in the boring function of the cannula as it enters bone.

In still further non-limiting embodiments aspects of the invention, relate to medical devices and their uses for accessing intraosseous space and delivering agents thereto. In certain of these embodiments, the devices have an elongated tubular member having a proximal end and a distal end; at least one lumen extending through the elongated tubular member having a proximal opening and a distal opening; a luer lock having at least a proximal end, a distal end, an internal channel extending through the luer lock between the proximal end and the distal end, and permanently attachable to the proximal end of the elongated tubular member; the luer lock further has an external wall having at least two slots therein extending from the proximal end of the luer lock toward the distal end of the luer lock coaxially with the internal channel of the luer lock; the luer lock still further has at least two luer lock projections projecting radially from the luer lock wall proximate the luer lock proximal end; in embodiments, the devices may further have an elongated wire with a proximal end and a distal end, the elongated wire slidably engageable within the lumen of the elongated tubular member; a drill stop having a distal end, a proximal end, and a channel within the drill stop extending between the proximal end and the distal end, the drill stop channel slidably engageable over the elongated wire, and permanently attachable to the elongated wire; and, for example, the drill stop further having at least two drill stop extensions extending distally from the distal end of the drill stop and coaxially with the drill stop channel, the drill stop extensions reversibly insertable within the slots of the luer lock when the distal end of the drill stop is proximate the proximal end of the luer lock.

Further embodiments of the invention include, for example, the above-described medical devices (e.g., but not limited to those of the preceding paragraph) further having a luer lock handle; the exterior of the luer lock handle potentially having external gripping features.

Still further, but not by way of limitation, non-limiting examples of embodiments of the present invention include certain embodiments discussed above, for example but not limited to those discussed in the two preceding paragraphs, further having a luer lock cap with at least a proximal end, a distal end, a proximal end wall having at least one elongated wire opening therein, the elongated wire opening slidably receivable of the elongated wire, an internal threaded chamber and a distal opening of the internal threaded chamber at the distal end of the luer lock cap, the internal threaded chamber reversibly receivable of the drill stop and at least a proximal portion of the luer lock including the luer lock projections and reversibly threadable over the projections of the luer lock to reversibly hold the distal end of the drill stop against the proximal end of the luer lock, the extensions of the drill stop in the slots of the luer lock, and the elongated wire within the elongated tubular member.

Moreover, embodiments of the invention include certain of the medical devices discussed above further having a proximal exterior region of the luer lock at and near the proximal end of the luer lock, and a luer lock handle distal to the proximal exterior region, the external diameter of the proximal exterior region being less than the external diameter of the luer lock handle.

Yet further, potentially any or all of the components and devices discussed herein in the various embodiments of the invention (whether expressly identified as so or not) may be made of materials such as and including, for example but not by limitation, metals, polymers, composites, ceramics, and any combinations thereof.

Still further, but not by limitation, in embodiments where the at least the drill stop is permanently attached to the stylet or the luer-type lock is permanently attached to the cannula, such attachment may (but must not) be made by welding, adhesives, molding in the formation of the components, and combinations thereof.

BRIEF DESCRIPTION OF THE DRAWINGS

So that the above recited features and advantages of the disclosure can be understood in detail, a more particular description of the disclosure, briefly summarized above, may be had by reference to the embodiments thereof that are illustrated in the appended drawings. It is to be noted, however, that the appended drawings illustrate only illustrative embodiments of this disclosure and are, therefore, not to be considered limiting of its scope. The figures are not necessarily to scale, and certain features and certain views of the figure may be shown exaggerated in scale or in schematic in the interest of clarity and conciseness.

FIG. 1 is a perspective view showing an assembled device including a cannula, a stylet, a handle luer lock, and a luer lock cap.

FIG. 1A is a perspective view showing the cannula of FIG. 1 and the attached handle luer lock of FIG. 1. The handle of the handle luer lock is partially cutaway.

FIG. 1B is a perspective view showing the stylet of FIG. 1 and an attached drill stop.

FIG. 3B is side view of the drill stop of FIG. 3 showing the drill stop extensions as vertical.

FIG. 3C is an end view of the proximal end of the drill stop of FIG. 3.

FIG. 5 shows, in part, that the simple luer lock does not have a handle, as with the handle luer lock shown in FIGS. 1, 1A, 1D, and 2-2D.

DETAILED DESCRIPTION

Figure 1C:
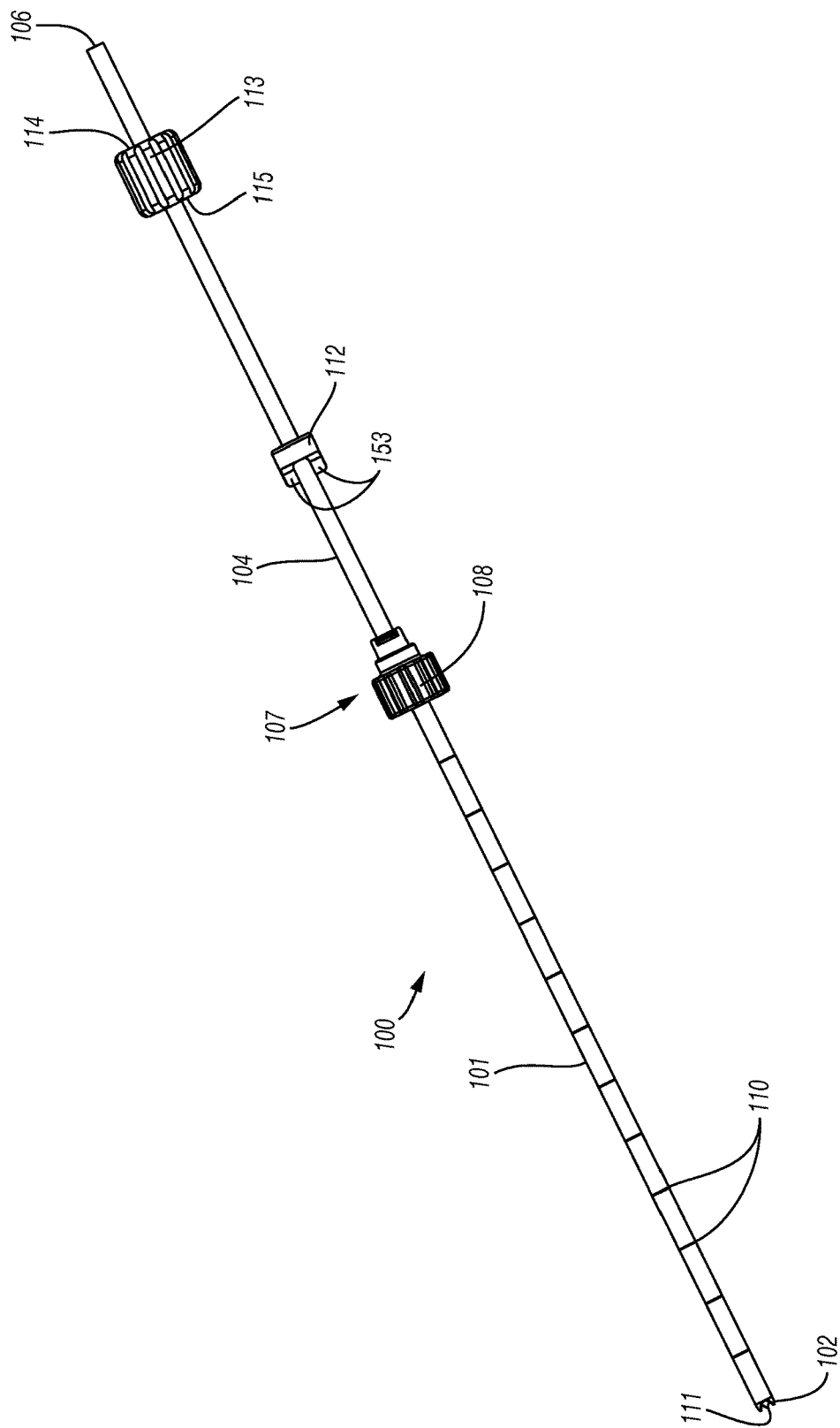
FIG. 1C shows a perspective view of the assembled device of FIG. 1, wherein the stylet is partially inserted into the cannula and into the handle luer lock, and the luer lock cap is slidably engaged with the stylet, each of FIG. 1. Attached to the stylet, is a drill stop.

The description that follows includes exemplary apparatuses, devices, materials, methods, techniques, and the like that embody techniques of the inventive subject matter. However, it is understood that the described embodiments may be practiced without these specific details and that the invention is not necessarily limited to these details.

Before the present invention is described in detail, it is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process act(s) or step(s), to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "and," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs.

FIG. 1 shows an exemplary perspective view an embodiment 100 of the invention wherein an elongated tubular member or cannula 101 houses elongated wire or stylet 104. The elongated tubular member 101 has a distal end 102, a proximal end (not shown in FIG. 1), and a lumen (not shown in FIG. 1) for slidably and reversibly receiving elongated wire 104. The lumen for the stylet 104 may the sole lumen of the cannula 101 or may be one of two or more lumina of the elongated tubular member 101. The elongated wire 104 has a distal end 105 and a proximal end 106.

The proximal end of cannula 101 (not shown in FIG. 1) has attached to and/or into it a handle luer lock (handle luer-type lock) (not shown in full in FIG. 1), including a handle 108.

In the embodiment 100 shown in FIG. 1, the elongated tubular member or cannula 101 houses the elongated wire or stylet 104 such that the wire 104 is reversibly coupled (as shown in detail below) to the cannula 101 by reversible interactions of the handle luer lock affixed to the proximal end of tubular member 101 with at least a drill stop (not shown in FIG. 1) and/or a luer-type lock cap 109. As shown in more detail below, luer lock cap 109 has at its proximal end (not shown in FIG. 1) an opening large enough to clear the outer diameter of elongated wire 104 yet small enough to retain the outer diameter of a drill stop (not shown in FIG. 1) attached to stylet 104 at a desired location for coupling of the wire to the cannula. Luer cap 109 is threadably engageable with the handle luer lock in order to reversibly couple stylet 104 with cannula 101 (shown in more detail below). FIG. 1 also shows optional depth markers 110 on the exterior of tubular member 101. These may be used, for example, by a medical professional in determining and/or confirming the depth to which tubular member 101, and/or the stylet 104 within the lumen of tubular member 101, have been inserted into a patient (e.g., into a patient's bone).

In all of the various embodiments, and variants thereof, of the invention described throughout this disclosure, components of the device, and of the components of the device to be used in the methods of the invention, may be supplied in the form of kits having various combinations and subcombinations of the components disclosed herein for these devices. For example only, various combinations of some or all of the components in each and all of the embodiments described herein may be provided in kit form (and of varying combinations and subcombinations as described herein). Kit aspects of the invention are described herein in exemplary reference only by referring to an extent to the embodiment 100 as shown in FIGS. 1-1C. However, it is expressly noted that kits are described and disclosed for each and all of the other embodiments of the inventions disclosed herein, and all variants thereof.

With reference to the embodiment 100, for example, shown in FIGS. 1-1C, kits containing combinations of the following components, and subcombinations thereof are a part of the embodiments of the invention: an elongated tubular member or cannula 101, an elongated wire or stylet 104 (each substantially as described herein and shown in FIGS. 1-1C) for example, the elongated tubular member 101 having a distal end 102 and a proximal end, and a lumen inside of the cannula for slidably and reversibly receiving elongated wire 104. In some of the kits of the invention, the lumen for the stylet 104 may, for example, be the sole lumen of the cannula 101; however, it may also be one of two or more lumina of the elongated tubular member 101. Further, the elongated wire 104 has a distal end 105 and a proximal end 106.

Figure 2:
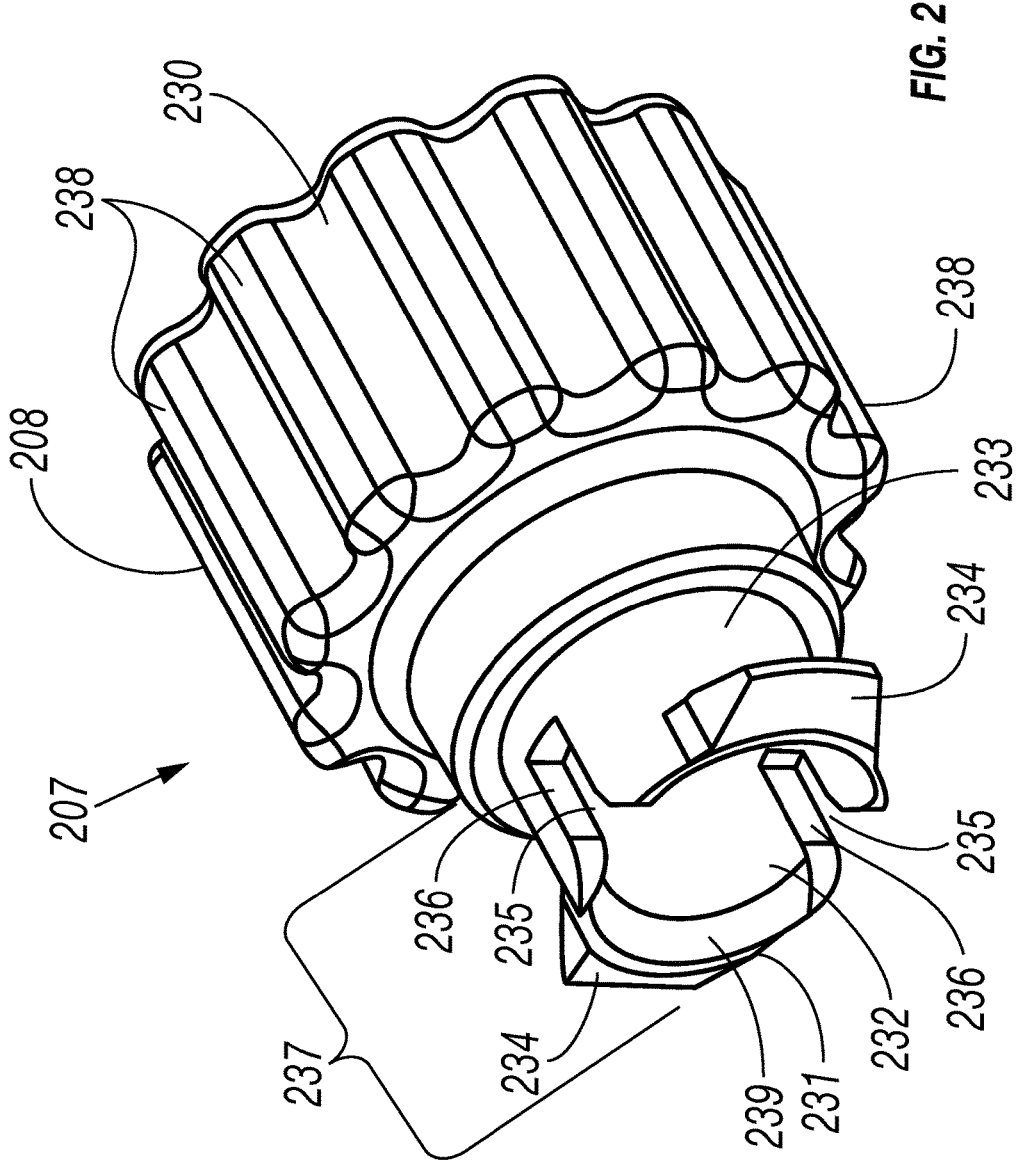
FIG. 2 is a perspective view showing the handle luer lock.
Figure 2A:
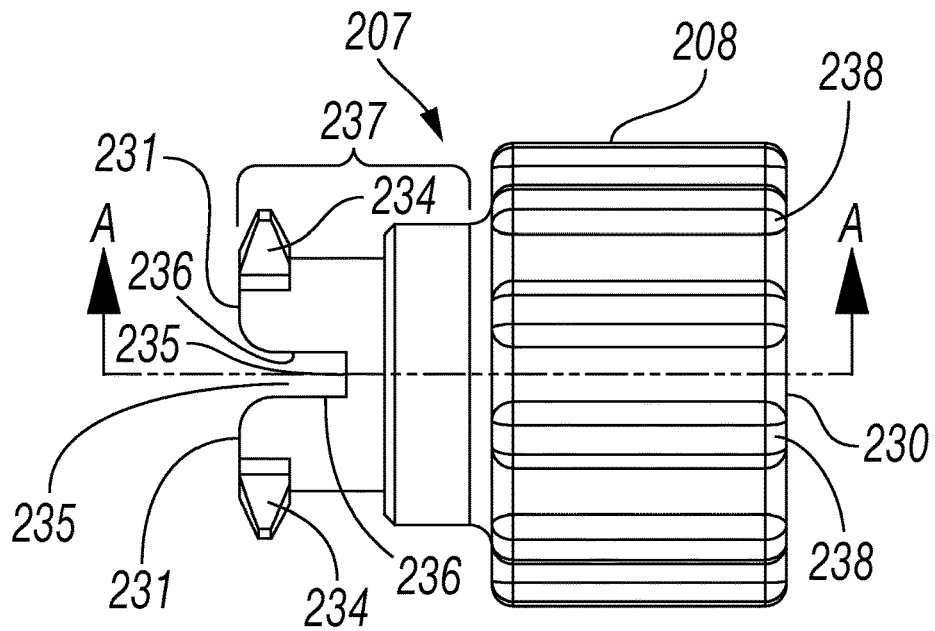
FIG. 2A is a side view showing the handle luer lock of FIG. 2 and the cross section A-A of FIG. 2B.
Figure 2B:
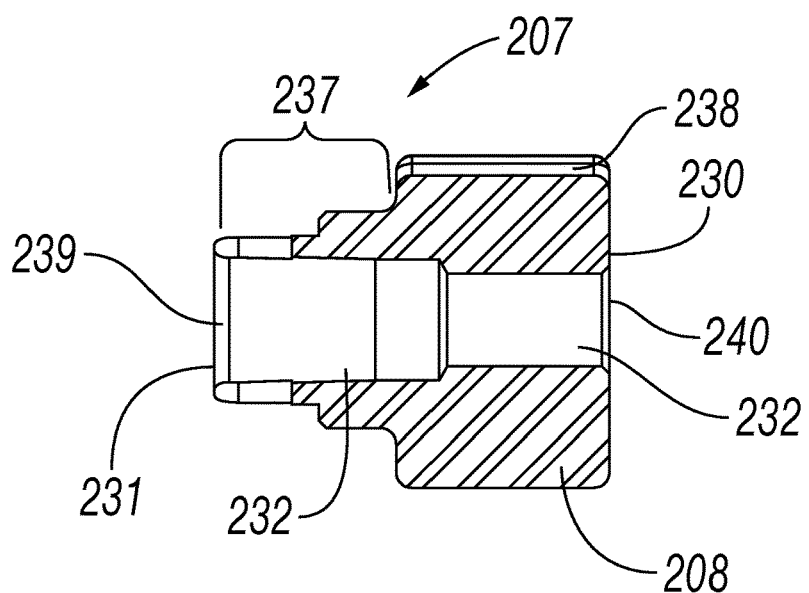
FIG. 2B is a cross sectional view of the handle luer lock of FIG. 2 along the cut A-A shown in FIG. 2A.
Figure 2C:
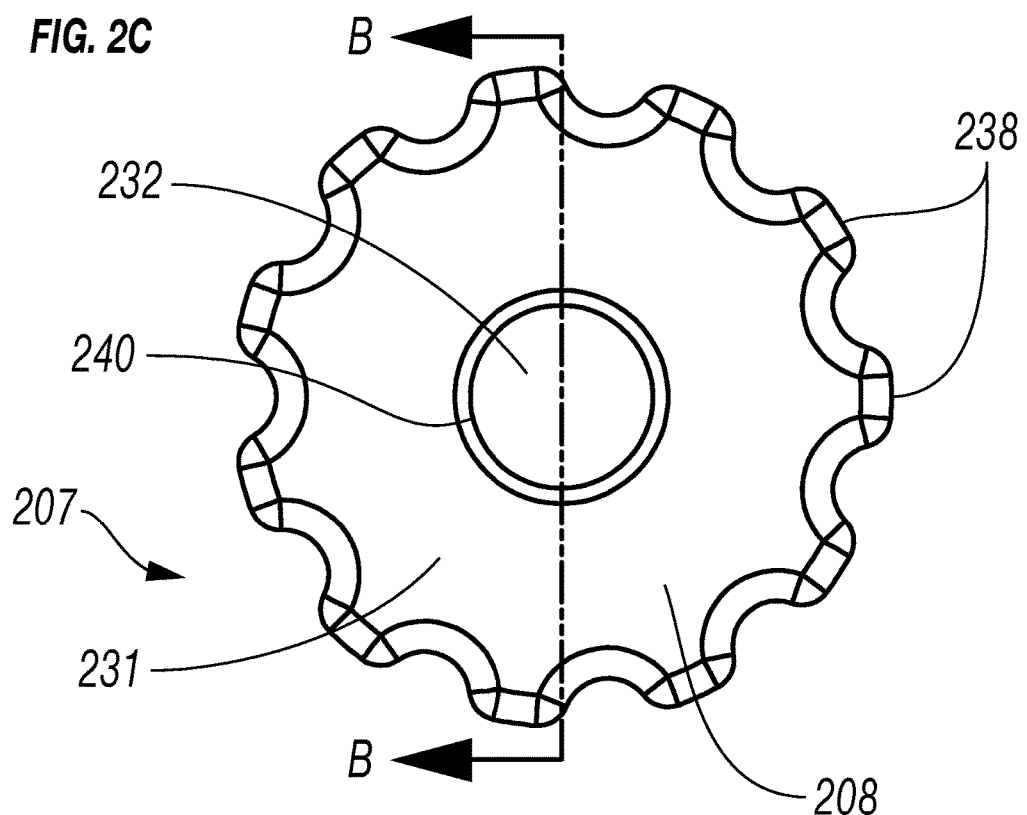
FIG. 2C is an end view, looking toward the distal end of the handle luer lock of FIG. 2. Also shown is the cross section line B-B, which forms the basis of the cross sectional view of FIG. 2D.
Figure 2D:
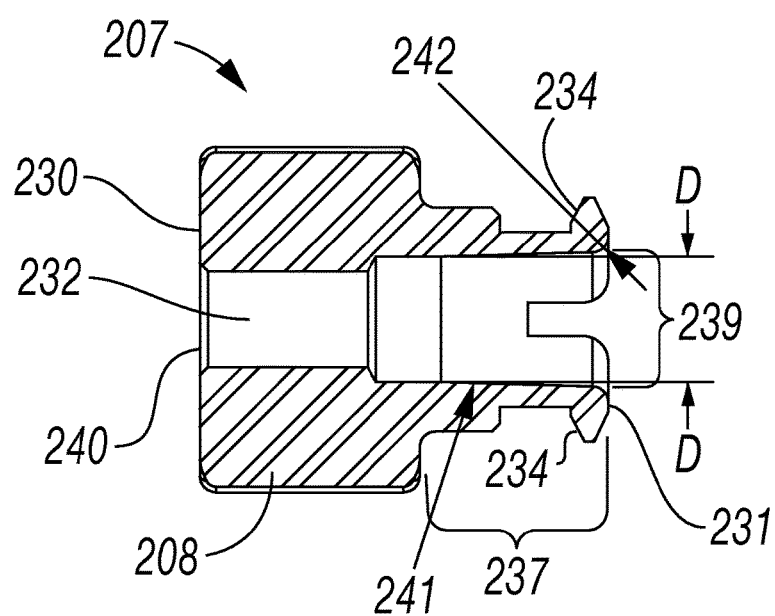
FIG. 2D is a cross sectional view of the handle luer lock of FIG. 2, along the cut B-B shown in FIG. 2C.
Figure 5:
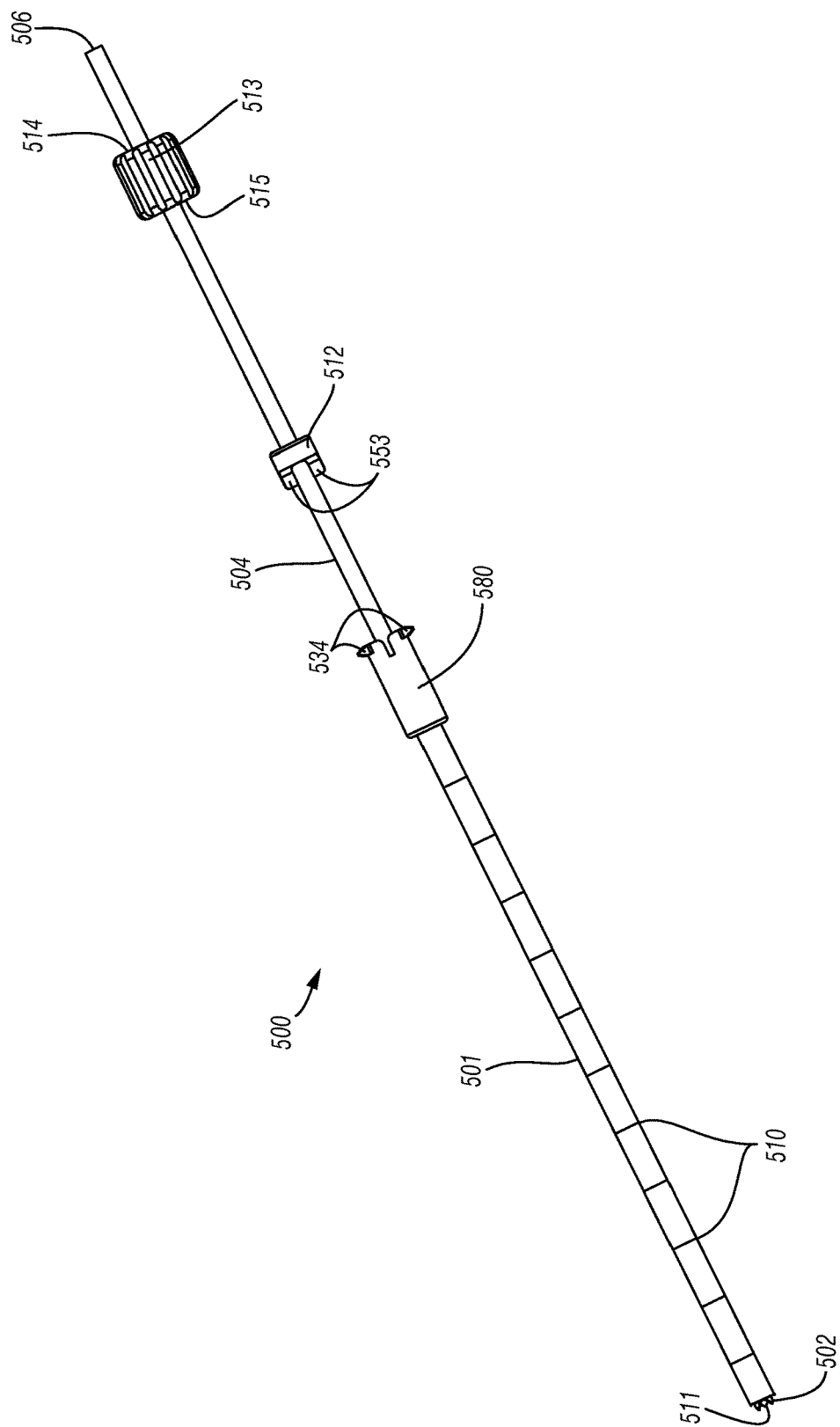
FIG. 5 is a perspective view of the simple luer lock, shown in partial assembly with the cannula, stylet, drill stop, and luer lock cap.
Figure 5A:
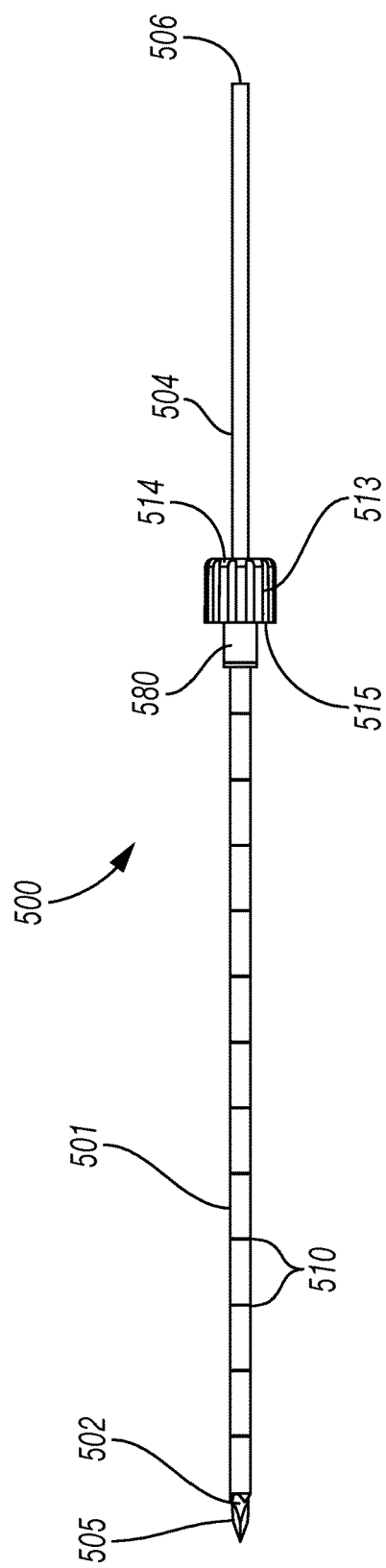
FIG. 5A is a perspective view of the assembled device of FIG. 5.
Figure 5B:
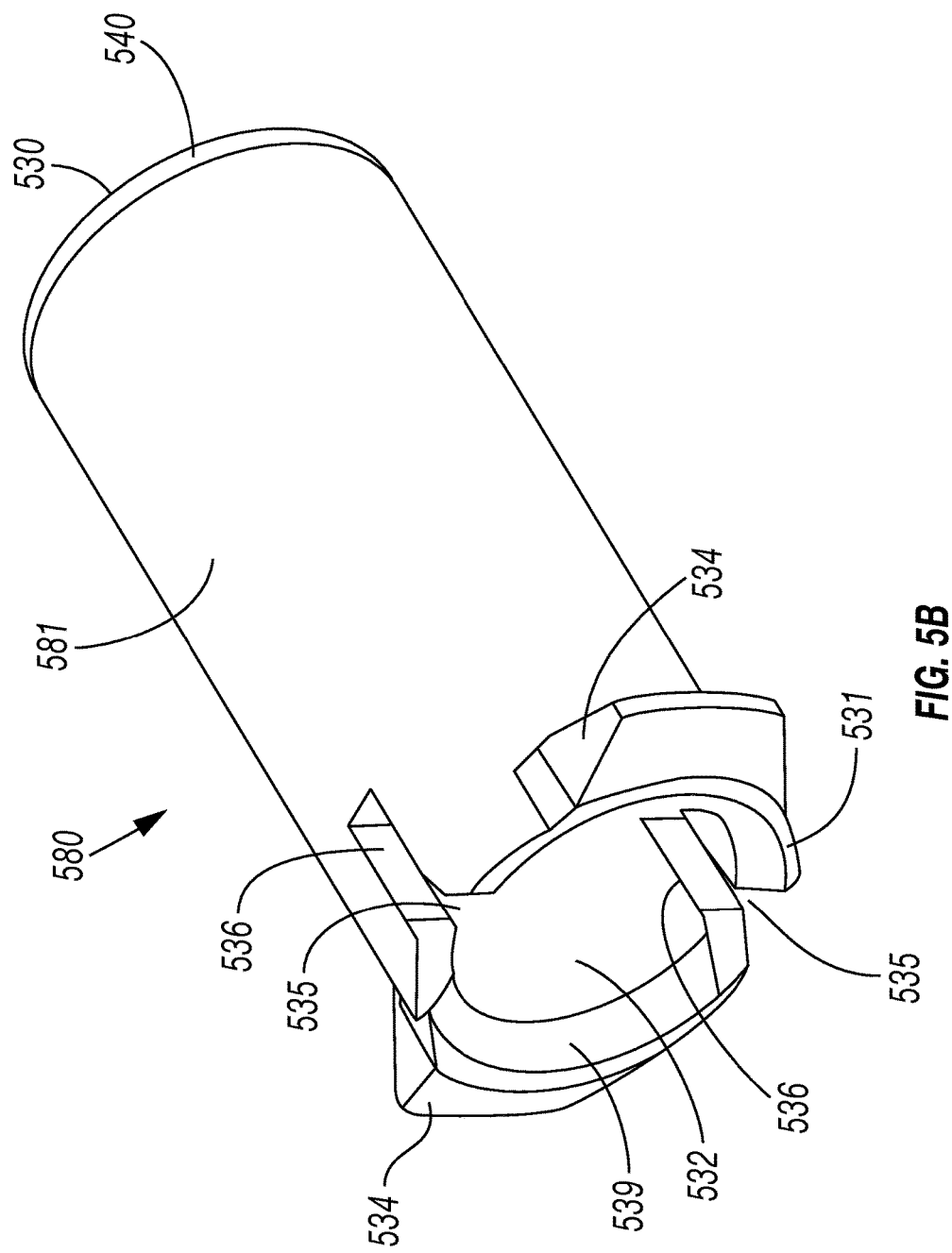
FIG. 5B is a perspective view of the simple luer lock.
Figure 5C:
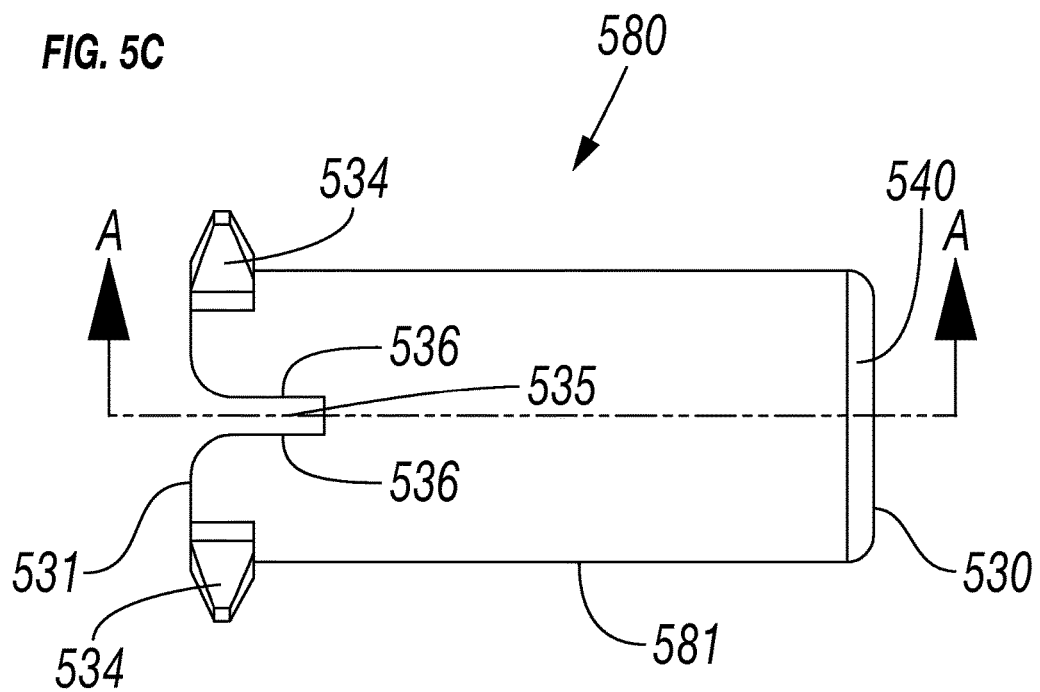
FIG. 5C is a side view of the simple luer lock. Also shown is the cross section line A-A, which forms the basis of the cross sectional view of FIG. 5D.
Figure 5D:
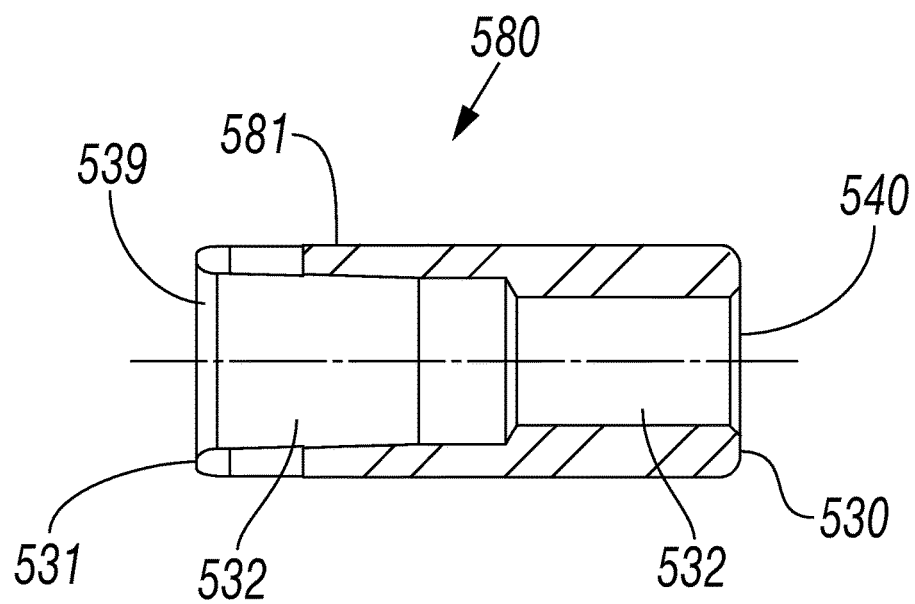
FIG. 5D is a cross sectional view of the simple luer lock along the cut A-A shown in FIG. 5C.
Figure 5E:
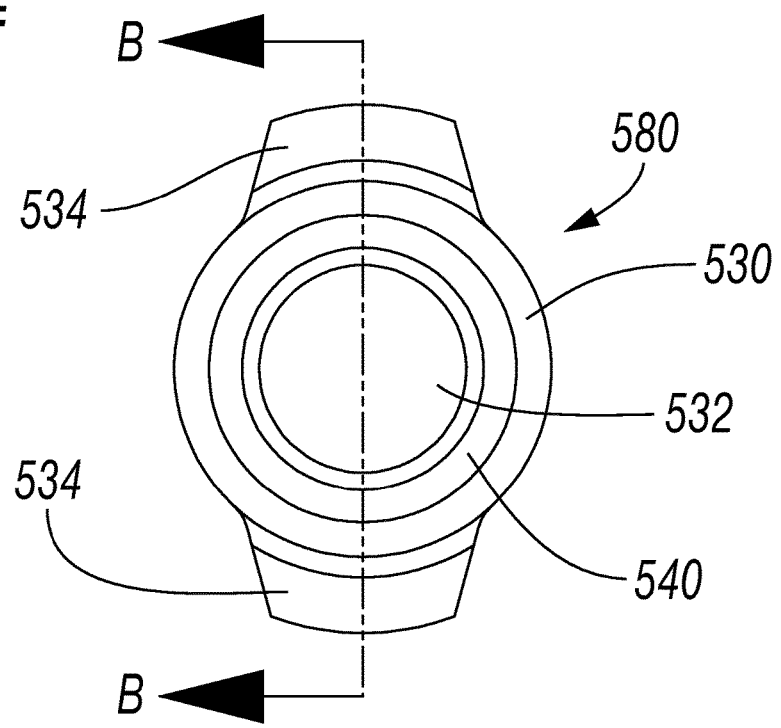
FIG. 5E is an end view, looking toward the distal end of the simple luer lock. Also shown is the cross section line B-B, which forms the basis of the cross sectional view of FIG. 5F.
Figure 5F:
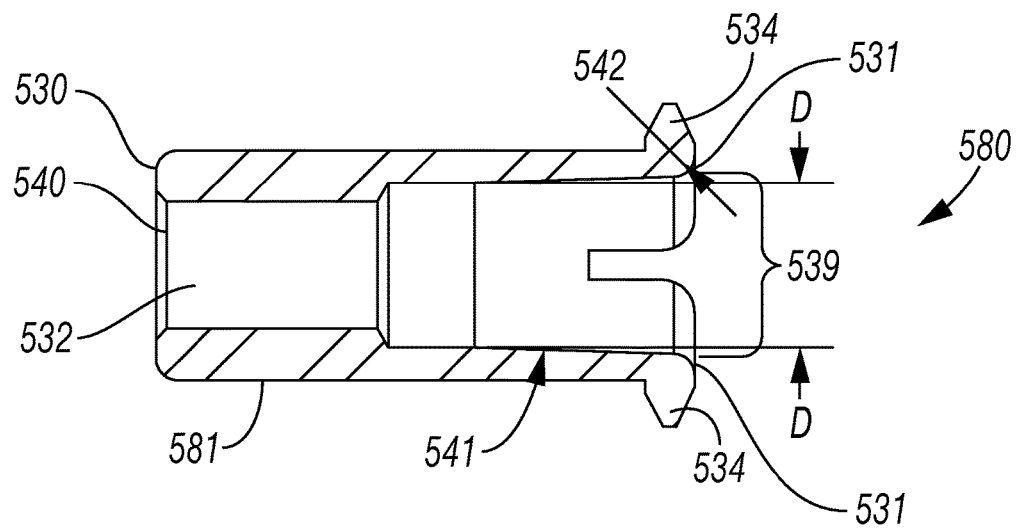
FIG. 5F is a cross sectional view of the simple luer lock along the cut B-B shown in FIG. 5E.

The cannula 101 as supplied in certain embodiments of the kit has attached to and/or into it a luer lock that has been modified as discussed in shown in FIGS. 2-2D (e.g., having luer lock slots 235 added thereto) wherein the luer lock may or may not have a luer lock handle 108 (e.g., compare FIGS. 1-1C and 2-2D with FIGS. 5-5F).

In the embodiments of the invention, the wire 104 is reversibly coupled (as shown in detail below) to the cannula 101 by reversible interactions of the luer lock (handle or simple) affixed to the proximal end of tubular member 101 with at least a drill stop having extensions 153 to mate within the luer lock slots 235 (and slot walls 236) which may also be included in a kit, such as those described above (and throughout; e.g., 112 of FIG. 1B). A kit as described herein may also include a luer-type lock cap 109. As shown in more detail below, luer lock cap 109 has at its proximal end an opening large enough to clear the outer diameter of elongated wire 104 yet small enough to retain the outer diameter of a drill stop attached to stylet 104 at a desired location—allowing for coupling of the wire to the cannula via the drill stop extensions 153 into luer lock slots 253. Where present in a kit, luer cap 109 is threadably (but optionally as, for example, engagement of the drill stop extensions on the wire and slots in the luer lock/cannula can occur without the luer lock cap) engageable with the luer lock in order to reversibly couple stylet 104 with cannula 101. FIG. 1 also shows optional depth markers 110 on the exterior of tubular member 101. These may be included on the tubular member of certain embodiments of kits of the invention, and may be used, for example, by a medical professional in determining and/or confirming the depth to which tubular member 101, and/or the stylet 104 within the lumen of tubular member 101, have been inserted into a patient (e.g., how far inserted into a patient's bone).

In a non-limiting, exemplary embodiment, a kit of the present invention may include: (1) cannula 100 (having a modified luer lock at its proximal end); (1) stylet 104 (having a drill stop 112 attached to it); and (optionally) (2) luer caps 109. This kit may further, optionally, include (1-3, preferably 3) negative mating (female) luer-to-luer connectors (for connecting syringes, e.g., if necessary in mixing a component to be injected into a BML) and/or (1-3, preferably 3) 3 ml syringes.

FIG. 1A shows an exemplary perspective view of the elongated tubular member or cannula 101 of the embodiment 100 shown in FIG. 1. The elongated tubular member 101 has a distal end 102, a proximal end 103, and depth markers 110. The figure also shows optional teeth 111 arranged about the cylindrical trocar like distal end 102 of tubular member 101. Optional teeth 111 may assist the cannula, with or without the distal end 105 of stylet 104 projecting from the distal end 102 of cannula 101, in drilling into bone when the cannula 101 (and stylet 104 if coupled with cannula, as discussed below) is rotated about its axis (e.g., in a drilling motion).

FIG. 1A also shows handle luer lock 107, including a partial cutaway in the handle 108 of handle luer lock 107 which shows the location of the proximal end 103 of cannula 101 within the embodiment 100 of FIG. 1. As discussed below, the proximal end 103, and/or an area near proximal end 103 of cannula 101 is firmly and irreversibly attached, over at least the lifetime of the device, to the handle luer lock 107 as shown for example in FIG. 1A. The attachment of the cannula to the luer lock may be made by welding, for example, between two metal parts, (e.g., between a solid steel cannula and a solid steel luer lock (luer-type lock) (of all stainless steel or, e.g., having at least a portion of stainless steel in an area for a welding attachment to the cannula (e.g., a solid steel cannula attachment lining)). The luer lock and cannula may be irreversibly attached (over at least the lifetime of the instrument) by other ways known or knowable in the art, such as by a strong, substantially permanent biocompatible adhesives (glues), co-molding of the same substance, etc.

FIG. 1B shows the elongated wire or stylet 104, including its distal 105 and proximal 106 ends. The figure also shows drill stop 112, having drill stop extensions 153, both of which are described in more detail below. The distal end 105 of stylet 104 shown in FIG. 1B is pointed. It is also within the scope of the invention that the distal end of the stylet be of other configurations than that shown in FIG. 1B, for example, sharp but in different configurations (e.g., pointed, having different numbers of sides, etc.), blunt, diamond tipped, and so forth as known and knowable to those in the art.

FIG. 1C shows a perspective view of the partially assembled handle luer lock device of FIG. 1, wherein the elongated wire or stylet 104 is partially inserted into a lumen (not shown in FIG. 1C) of elongated tubular member or cannula 101. The cannula has distal end 102 with teeth 111. The figure further shows the handle luer lock 107, including the handle section 108, affixed to the proximal end of the cannula 101 (shown and discussed in more detail below). The figure further shows the drill stop 112, with drill stop extensions 153, affixed to a desired site on stylet 104. As discussed herein, in embodiments of the invention, the drill stop 112 is firmly attached (permanently attached over the lifetime of the instrument, which may be single or multiuse; e.g., by welding) to the stylet 104 at a location that ensures that the stylet is at a desired position within the cannula of the assembled device (e.g., as shown in FIG. 1). For example, where it is desirable that in the coupled assembly (as shown, for example in FIG. 1; e.g., prior to and/or during insertion (e.g., by drilling), for example, into an intraosseous space) the distal end 105 of the stylet 104 extend a certain length beyond (distal to) the distal end 102 of the cannula 101, for example as shown in FIG. 1, the drill stop 112 is located at a position on the stylet 104 such that when the stylet and cannula are coupled (e.g., when the handle luer-type lock 107 is threadably coupled with the luer lock cap 113, the drill stop 112 is held within the drill cap 113 (and against the proximal end of the luer lock, as discussed in more detail below)) the length of stylet 104 extending distally from the drill stop 112 positions the elongated wire within the assembly 100 to project from the distal end 102 of the cannula 101 by a desired length. Embodiments where the drill stop is used to position the distal end of the stylet beyond the distal end of the cannula may be desirable when, for example, the distal end of the stylet is pointed or otherwise sharp and may be used to aid in positioning the device, for example, in initially drilling through outer bone (and/or to aid the direction of traversing of the device within bone). In such cases, a sharpened or pointed stylet tip may be used to create an initial pilot hole in a surface of a bone where drilling is desired. Because of the sharpness of the stylet end, it may readily form such a hole, assisting a surgeon in initiating drilling at a precise location on the surface of a bone and in maintaining the location of the bore when drilling with the full device (e.g., with sharp and/or pointed distal end of a stylet and a trocar-like circular cutting end (with or without teeth) at the distal end of the cannula). This is believed, but not by limitation, to help overcome and/or alleviate problems known in the art such as sliding, skipping, and skidding when a bone marrow access instrument is used to initiate a drill hole at a desired location on the surface of a bone. It is further believed, but not by limitation, that such use may assist a surgeon or other medical professional in guiding the device to a desired, precise location within an intraosseous region of a bone (e.g., a BML).

Embodiments where the distal end of the stylet may for example be blunt, and/or where for any reason it is not desirable for the stylet to form the distal end of the assembled device, may have the drill stop located on the stylet such that when the stylet is coupled with the cannula, the distal end of the stylet may be flush with, or recessed from, the distal end of the cannula.

FIG. 2 shows a perspective view of a handle luer lock 207, including a handle 208 having external gripping features 238, a proximal end 231, a distal end 230, and a channel 232 extending axially through handle luer lock 207.

Also shown in FIG. 2 are two (yet, some embodiments of the invention may contain one, or more than two) luer-type lock projections 234 at or near the distal end 231 that extend radially or substantially radially from the axis of the handle luer-type lock 207 from or near the proximal end 231 of luer lock 207.

FIG. 2 further shows a channel 232 that opens to both the distal end 230 and the proximal end 231 of luer lock 207. The channel 232 extends axially through the luer-type lock 207, between the openings at the proximal and distal ends of the handle luer lock 207. As shown below, the channel 232 is substantially cylindrical, yet the diameter of the channel may change within the luer lock. FIG. 2 also shows the proximal opening 239 of channel 232.

Additionally, FIG. 2 shows slots 235; having sides 236, within a proximal region 237 of handle luer lock 207. As shown in the embodiment in FIG. 2, the proximal region 237 has two slots opening to the proximal end 231 of the luer lock 207, with one slot located between each projection 234 (however, alternative numbers of slots, and/or projections and/or locations for either are within the scope of this invention and disclosure herein). The slots 235 are defined by slot sides 236, that are cut through handle luer lock proximal region wall 233 such that each slot extends axially, or substantially axially, into the wall 233 of the proximal region 237 of the luer lock (luer-type lock) 207. As discussed below, in embodiments of the invention, slots 235 reversibly receive extensions (not shown in FIG. 2) of the drill stop when reversibly coupling the stylet and the cannula. Also, and as discussed elsewhere herein, as an additional aspect of reversibly coupling the stylet to the cannula, the projections 234 reversibly threadably engage with internal threads in the luer-type lock cap 113 (not shown in FIG. 2) so that the cap, retaining the drill stop, may be threaded over the proximal region 237 by threading over projections 234 thus reversibly securing the engagement of the drill lock, affixed to the stylet, with luer lock, affixed to the lumen; thereby, reversibly coupling the lumen and stylet (uncoupling may be done, for example, by unscrewing the luer cap from the luer lock and removing the extensions of the drill stop from the slots in the handle luer-type lock).

FIG. 2A is a side view of the handle luer lock 207. Similar to FIG. 2, the handle luer lock 207 in this figure has a handle 208 with external gripping feature 238 (such as a gripping thread or other physical traction aid), a distal end 230, proximal end 231, and proximal end region 237. The figure further shows projections 234, slot 235, and slot sides 236. FIG. 2A also shows the cross section line A-A, which extends axially through the luer-type lock 207, and which forms the basis of the cross sectional view of FIG. 2B.

FIG. 2B a cross sectional view along the cut A-A shown in FIG. 2A. FIG. 2B shows the handle lure lock 207, a luer lock handle portion 208 with external gripping feature 238, a distal end 230, proximal end 231, a proximal end region 237, and channel 232 which passes axially through the luer lock 207 and between a proximal opening 239 and distal opening 240. In the embodiment shown in FIG. 2B, the internal diameter of the channel 232 is smaller toward the distal end of the luer lock 207 than toward the proximal end. However, as discussed below, the internal diameter of the channel toward the distal end must allow the external diameter of a cannula (e.g., of cannula 101, including at its proximal end 103 as shown, e.g., in FIG. 1A) to fit securely within the channel for permanent (over the lifetime of the device) attachment to the handle luer lock. The internal diameter of the channel 232 throughout the handle luer lock 207 must allow the external diameter of the stylet (e.g., stylet 104 of FIG. 1B) to reversibly pass through the channel 232 (and reversibly into a lumen of the cannula 101).

FIG. 2C is an end view, looking toward the distal end 230 of handle luer lock 207, specifically toward the distal end of the handle 208 of the luer lock 207. External handle gripping threads 238 are also shown, as is the distal opening 240 of the channel 232.

FIG. 2C also shows the cross section line B-B, which forms the basis of the cross sectional view of FIG. 2D.

FIG. 2D a cross sectional view along the cut B-B shown in FIG. 2C. FIG. 2D shows the handle lure lock 207, a luer-type lock handle portion 208, a distal end 230, proximal end 231, a proximal end region 237, and channel 232 which passes axially through the luer lock 207, between a proximal opening 239 and distal opening 240. In the embodiment shown in FIG. 2D, the internal diameter of the channel 232 is smaller toward the distal end of the luer-type lock 207 than toward the proximal end. However, the internal diameter of the channel toward the distal end must allow the external diameter of a cannula (e.g., 101) to fit within the channel (and be affixed therein) and the internal diameter of the entire channel 232 must allow the external diameter of the stylet (e.g., 104) to pass through the channel (and into the lumen of the cannula).

FIG. 2D also shows an outward taper 241 in the internal diameter of the channel 232. This may be useful, for example but not by limitation, in engaging the outer diameter of the proximal end 103 of the cannula 101 within the channel 232 (not shown in FIG. 2D; but see, e.g., FIG. 1B). Also shown in FIG. 2D is a chamfer 242 located proximate the proximal end 231 of the luer-type lock channel 232 opening 239. This chamfer allows for the internal diameter of the channel 232 to further increase beyond that of the taper 241 proximate the proximal opening of the channel 232. Like the taper, the chamfer may also, for example but not by limitation, assist in inserting and engaging the proximal end 103 of the cannula 101 into the proximal opening 239 of channel 232 of the handle luer lock 207 (see, e.g., FIG. 1A).

The taper and chamfer shown for the channel 232 in FIG. 2D may also apply to any or all channels, chambers, openings, and the like disclosed herein.

As discussed below, the distal end 103, and/or an area proximate the distal end 103 of cannula 101 is firmly, and irreversibly over the lifetime of the instrument, attached to the handle luer lock 207 at, for example, the location shown in FIG. 1A (briefly, a region within and toward the distal end of channel 232 of the luer-type lock 207). The attachment of the cannula to the luer lock may be made by welding (e.g., between two metal parts, e.g., between a solid steel cannula and a solid steel luer lock (of all stainless steel or, e.g., having at least a portion of stainless steel in an area for a welding attachment to the cannula (e.g., a solid steel channel lining)), and by another way known or knowable in the art. For example, but not by limitation, the luer lock (luer-type lock) and cannula may be attachable by welding, strong, long lasting biocompatible adhesives (glues), by co-molding of the parts together, mechanical interference connection such as a press fit spline and the like.

Figure 3:
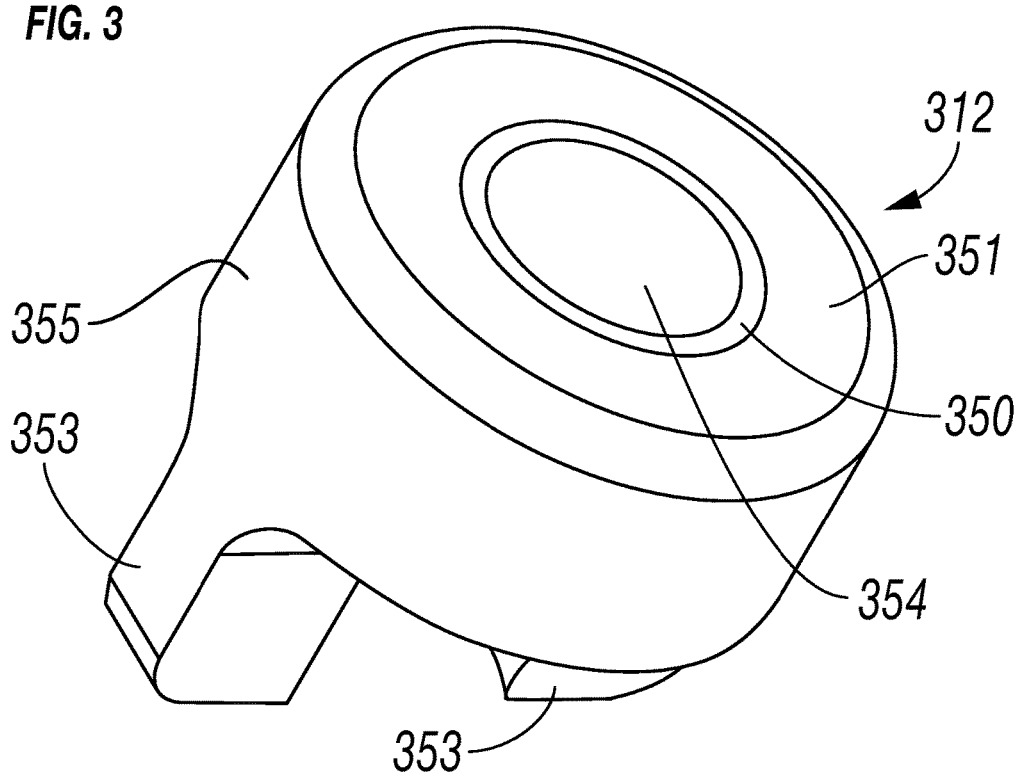
FIG. 3 is perspective view of the drill stop, including partial views of the drill stop extensions.

FIG. 3 is perspective view of drill stop 312 showing a proximal opening 350 in a proximal end 351 that opens into a stylet containment region 354. While not shown in FIG. 3, the end of the drill stop 312 opposite the proximal end is the distal end, which has a distal opening to stylet attachment region 354. The proximal 350 (and distal) openings and the stylet attachment region 354 are sized to slidably receive, and to be permanently attachable to, a stylet (e.g., stylet 104). As described in more detail elsewhere in this disclosure, the drill stop 312 is firmly attachable to a stylet (e.g., stylet 104), yet in some embodiments may be slidably engageable with the stylet before attachment. When a stylet is disposed within stylet attachment region 354, but is not firmly (e.g., permanently) attached to drill stop 312, it is slidably engageable with the drill stop 312 through the openings to and the stylet attachment region 354, which extends axially through the drill stop 312 between the proximal opening 350 and a distal opening.

As also shown in FIG. 3, the proximal opening 350 of the stylet attachment region 354 is chamfered and/or tapered. In embodiments of the invention, the chamfer provides for ready insertion, removal, and reversibility of the drill stop on a stylet, and provides for ready attachment of the drill stop to a stylet, for example, by welding.

Generally, any, all, or any number in between, of edges, edges of openings, and the like of any and/or all of the components of the medical devices herein (e.g., but not limited to, the handle luer lock device 100, and all component parts thereof (e.g., handle luer lock 207, drill stop 312 and luer lock cap 413)) may be tapered and/or chamfered. Chamfering and/or tapering may, for example but not by limitation, provide for ready coupling (including reversible and irreversible) and uncoupling and attachment or disassembly of the various components of any and/or all of the various components of the medical devices of the present invention.

A stylet may be attached to the drill stop 312 by any manner and material(s) known or knowable in the art. By non-limiting example, a metal drill stop (or a drill stop containing a weldable component, such as stainless steel, in the stylet attachment region) may be welded to a metal (e.g., stainless steel) stylet. The drill stop may also be attached to a stylet by biocompatible adhesives, including those causing permanent adhesion over the lifetime of the instrument (which may be single or multiple use devices). All other ways of attaching the stylet to the drill stop, known or knowable, are within the scope of this invention, including, for example, co-molding of the stylet and drill stop as, for example, a single unit (and, thus, inherently attached).

Additionally, FIG. 3 shows drill stop extensions 353 located radially about the axis of drill stop 312 and extending linearly, or substantially linearly from drill stop wall 355 at the distal end of the drill stop 312. In the embodiment of FIG. 3, the drill stop extensions 353 extend away from the drill stop 312 in the direction toward the distal end of the stylet that is attachable or attached to the drill stop (see, for example, FIG. 1B, showing drill stop 112, attached to (or slidably engaged with stylet 104, wherein the drill stop extensions 153 face toward the distal end 105 of stylet 104; see also, for example, FIG. 1D showing drill stop 112 attached to stylet 104 with drill stop extensions 153 facing toward cannula 101).

Figure 3A:
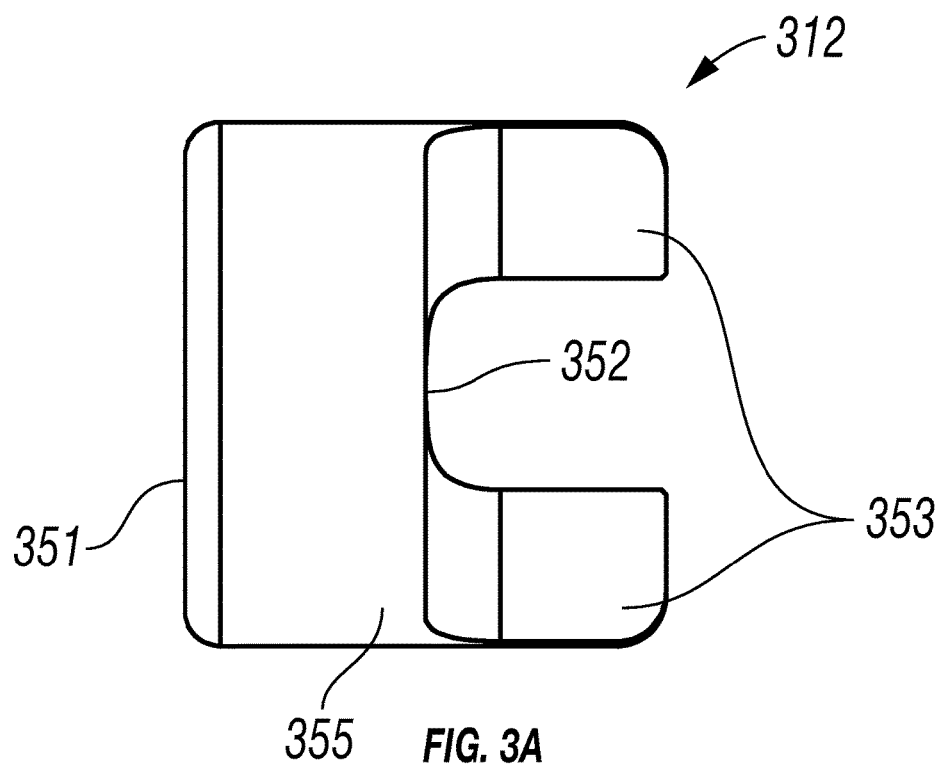
FIG. 3A is side view of the drill stop of FIG. 3 showing the drill stop extensions as horizontal.

In the embodiment shown in FIG. 3, drill stop 312 has two drill stop extensions 353 which extend distally from the distal end of the drill stop (see FIGS. 3A and 3B). The two drill stop extensions 353 of the embodiments of FIGS. 3-3B are located opposite each other and are extensions of the drill stop wall 355 (in alternative embodiments the drill stop extensions may be separate units from the drill stop wall; however, such extensions should be firmly engaged with the drill stop, for example, permanently attached (over the lifetime of the instrument) through the drill stop wall).

FIGS. 3A and 3B, discussed below, show additional details of the drill stop extensions 353. Further, and for example, as shown in and discussed for FIGS. 1B, 1D, 2, 2A, and 2D above, and as discussed throughout this disclosure, the drill stop extensions 353 are shaped to fit snugly but reversibly within slots cut axially into the proximal end of a handle luer lock (e.g., FIGS. 1B, 1D, 2, and 2D showing, respectively, handle luer locks 107 and 207, and FIGS. 2, 2A, and 2D slots 235 (with sides 236)). Therefore, and, for example, after the drill stop 312 has been permanently (or long term over, lasting more than the life of the instrument) attached to a stylet at a desired location, the distal end of a stylet is inserted into the proximal end a cannula (via the proximal end and opening of a handle luer lock attached to the proximal end of the cannula) until the drill stop extensions 353 reversibly but (within standard art tolerances) fully and snugly fit into corresponding slots in a luer lock. Due to the shape of the slots on the luer-type lock (see, for example, (e.g., FIGS. 1B, 1D, 2, and 2D showing, respectively, handle luer locks 107 and 207, and FIGS. 2, 2A, and 2D showing slots 235 and slot sides 236) and the corresponding shape of the extensions of the drill stop (see, e.g., FIGS. 3-3B), the drill stop extensions removably but firmly engage (generally fully, but it is within the scope of the invention that some tolerances are allowable) with the slots of the luer lock; however, the fit generally should not be so tight as to inhibit removal of the drill stop extensions from the slots when decoupling the stylet from the lumen (discussed below), including decoupling and coupling by manual force (discussed in more detail below). This snug but reversible fit couples the cannula (at or close to its proximal end, via the attached handle luer lock) to the elongated wire or stylet at the location of the drill stop on the stylet. In addition, the distal end of the drill stop generally, but not necessarily, fits snugly against the proximal end of the handle luer-type lock when the drill stop extensions are fully engaged within the luer lock slots.

When the drill stop extensions are reversibly inserted into the cannula slots, rotation of the stylet about the axis of the stylet causes concurrent or synchronized rotation of the cannula about the cannula's axis.

Further, the drill stop extensions 353 may be directly attachable with (to) a stylet. For example, the entire interior face of the stylet attachment region 354 of the drill stop 312, including that of extensions 353, may be affixed to (with) a stylet. Alternatively, the drill stop 312 may be attachable to a stylet only by the stylet attachment region 354. In such embodiments, the extensions are firmly associated with the stylet through, for example, attachment of the drill stop stylet attachment region 354 to a stylet and the firm association (for example, as being parts of the same unit) of the extensions and the drill stop 312.

The location of the drill stop 312 on a stylet provides, at least, a way for assuring that a certain amount of elongated wire or stylet is inserted into an elongated tubular structure or cannula (e.g., stylet 104 and cannula 101) when the elongated wire is coupled with the cannula, such as before (and after) insertion of the device into a bone. For example, the drill stop may be located such that when the device is assembled prior to use (for example, prior to drilling into a bone), a certain amount of a distal end (e.g., a sharp stylet end) of the stylet extends beyond the distal end of the cannula by a desired amount. This results in an assembled device having a stylet end as its penetrating end. In such embodiments, the leading distal tip of the stylet may provide for improved insertion of the device into bone; for example, in reducing or avoiding instrument skidding as the sharpened end of the stylet can quickly establish a small leading hole to initiate and guide insertion of the entire device at a desired location on a bone.

FIG. 3A is side view of drill stop 312, showing the drill stop viewed from a side wherein the drill stop extensions 353 are horizontal. The figure also shows the wall 355, and the proximal 351 and the distal 352 ends of the drill stop 312.

FIG. 3B is side view of drill stop 312, showing the drill stop viewed from a side wherein the drill stop extensions 353 are vertical. The figure also shows the wall 355, and the proximal 351 and the distal 352 ends of the drill stop 312.

FIG. 3C is an end view of the proximal end 351 of drill stop 312. The figure shows, for example, the proximal opening 350 of the stylet attachment region 354, and the wall 355 of the drill stop 312.

Figure 4:
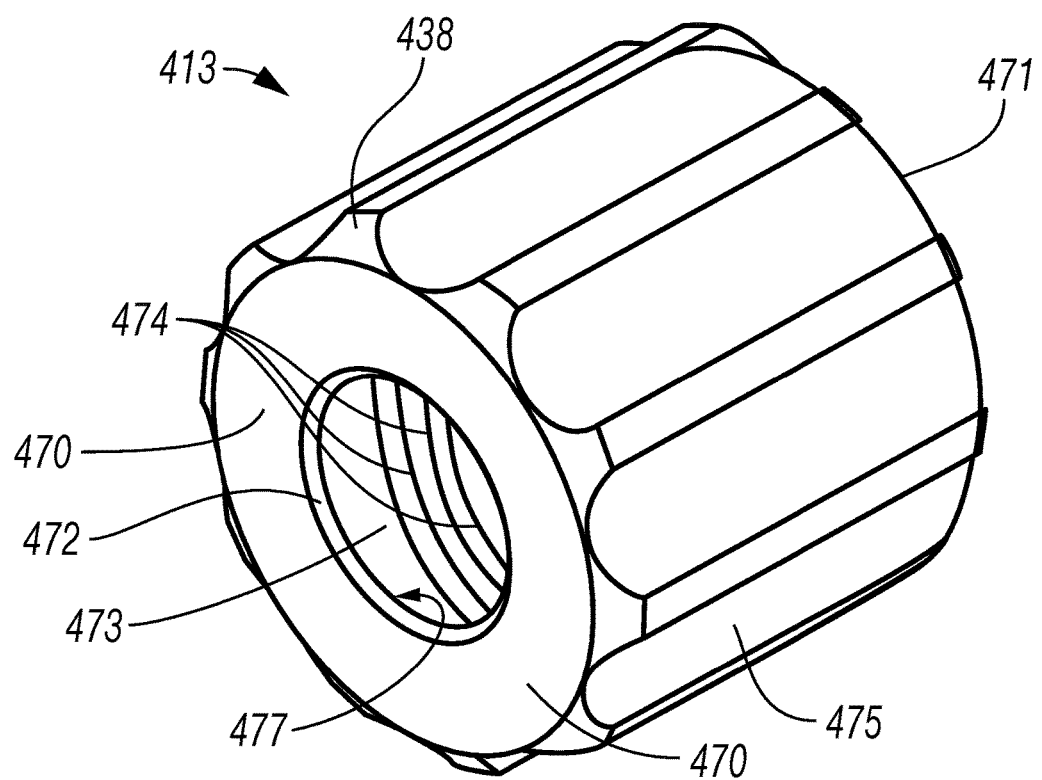
FIG. 4 is a perspective view of luer lock cap.

FIG. 4 is a perspective view of luer-type lock cap 413 (see also, e.g., 113). Luer lock cap 413 has proximal end 470, distal end 471, outer surface 475, and external gripping threads 438 on outer surface 475. The external gripping features 438 extend axially and parallel with each other about the outer surface 475 of the drill lock cap 413. The external gripping features 438 may assist in twisting (threading) the luer lock cap onto projections which project substantially perpendicularly from the axis of the device 100 (including from the axis of luer-type lock cap 413) of the handle luer lock 100 (see, e.g., 234).

FIG. 4 further shows internal threaded chamber 473 with internal threads 474, internal threaded chamber 473 extending the axial length of luer lock (luer-type lock) 413 between proximal through hole 472, and distal opening 476.

As described throughout herein, luer lock cap 413 fits over the proximal end of an elongated wire or stylet having a drill stop affixed to it at a desired location (preferably permanently affixed or at least affixed over the life of the device). The luer lock cap 413 firmly but reversibly couples an elongated wire or stylet with an elongated tubular member or cannula when the stylet has been inserted into the lumen of the cannula and (discussed in more detail below), and projections (e.g., 234) on a handle luer lock attached at the proximal end of the cannula (e.g., 234), the cannula having at least one lumen for slidably receiving the wire (stylet), are threadably engaged with internal threads within and beginning at the distal end of the luer lock cap.

More specifically, in embodiments of the invention, luer-type lock cap 413 is fitted over the proximal end of a stylet having a drill stop already (but not necessarily) attached thereto (see, e.g., stylet 104 with proximal end 106, and drill stop 312 attached thereto). In embodiments of the invention, when the luer lock cap 413 is fitted onto the stylet, the stylet is to be, is being, or has been, inserted into the proximal end of an elongated tubular member or cannula having at least one lumen for slidably receiving the stylet (see, e.g., stylet 104 with proximal end 106 and elongated tubular member 101 with proximal end 103). In still further embodiments, the stylet has affixed thereto, at a desired location, a drill stop (see, e.g., 112). Because the drill stop (e.g., 312) is located distal to the luer lock cap 413 and is to be held between the handle luer lock on the cannula and the cap 413, it may generally be most efficient to attach the drill stop to the stylet before assembling the device (e.g., before placing the luer lock cap 413 over the proximal end of the stylet). However, a drill stop may be attached to the stylet after the cap 413 has become engaged with at least the region proximate the proximal end of the stylet.

In embodiments of the invention, the distal end of the stylet may be inserted into the stylet receiving lumen of the cannula before, during, or after placing the cap 413 over the proximal end of the stylet.

As discussed and shown herein, the cannula has affixed at its proximal end a handle luer lock (see, e.g., 100). As also discussed herein, the handle luer lock is affixed proximate the proximal end of the cannula by any agents and/or procedures known or knowable in the art (including, for example, biocompatible adhesives and welding) to firmly affix the two components for at least the lifetime of the device 100 (which may be a single use or a multiuse device).

When a stylet having a drill stop affixed is inserted into a cannula having a handle luer lock affixed proximate or to its proximal end, drill stop projections (see, e.g., 353) which project distally and axially from the distal end of the drill stop (see, e.g., 352) reversibly engage with axial slots (see, e.g., 235 and slot walls 236) in the proximal end of the luer lock (see, e.g., 207) that is affixed proximate or to the proximal end of the cannula (see, e.g., 103), This engagement of the drill stop projections ("positive mating features") with the luer lock slots ("negative mating features") couples the cannula and the stylet together, as discussed below in more detail. One aspect of this coupling is that rotation of the stylet about its axis drives concurrent or synchronized rotation of the cannula (and vice versa).

Luer lock cap 413 assures that this coupling of the cannula and stylet is (but not by limitation): i) firm and complete (e.g., that the drill stop projections are fully inserted into the luer lock slots in a firm, but removable manner): and ii) only reversible upon unscrewing the lure lock cap, The luer lock cap 413 reversibly couples a cannula and stylet together by firmly, but reversibly, holding the distal end (including the projections) of the drill stop (affixed to the stylet) against the proximal end of the luer lock (affixed to the cannula). More specifically, the luer lock cap 413 reversibly retains within an internal threaded chamber 473 the proximal end of the drill stop by threadably engaging with projections that extend perpendicularly from the handle luer lock 207. Therefore, when the luer-type lock cap 413 is threaded on, the drill stop, including its extensions, are firmly held against the proximal end of the luer lock including the slots of the luer lock.

The luer lock cap 413 reversibly couples the cannula and stylet by internal luer lock cap threads 474 in internal threaded chamber 473 of luer lock cap 413 threading with luer lock extensions (see, e.g., 234) which extend perpendicularly from the axis and surface of handle luer lock (see, e.g., 207). The luer lock cap 413 is often, but not necessarily, manually tightened in order to reversibly hold the extensions of the drill stop into the slots of the luer lock on the cannula. Proximal stylet opening 472, located at the proximal end 470 of the luer lock cap, is of smaller dimension than the external diameter of the drill lock, but is of sufficient diameter that the stylet is slidably receivable within the proximal stylet opening. When the luer lock cap 413 is placed over the proximal end of a stylet having a drill stop (or having a drill stop to be affixed or affixing thereto), the cap is placed over the stylet in the orientation of the distal end of the cap 471 and the distal opening 476 of the luer lock cap 413 facing distally, toward the drill stop (which is located on the stylet distal to the cap). In this configuration, the luer-type lock cap is also oriented such that when the distal end of the stylet is inserted into the proximal end of a cannula having a luer-type lock at its proximal end, distal end 471 and the distal opening 476 of the luer lock cap 413 are facing distally toward, for example, the proximal ends of the drill stop, and luer lock, and the distal ends of the stylet and cannula.

Hence, the luer lock cap 413 may be slid distally down the elongated wire (stylet), with the wire entering the distal opening 476 of the cap, into the cap chamber 473 and exiting the cap by the proximal stylet opening, until the proximal end 477 of the luer lock cap chamber 473 meets the proximal end of the drill stop (see, e.g., 351). At this position, the proximal end of the drill stop on the stylet is contained within and is held against the proximal end 477 of the internal threaded chamber 473 of the luer lock cap 413. This is because the diameter of the proximal end of the drill stop is greater than the diameter of the proximal through hole of the luer-type lock chamber.

When the distal opening 476 of the luer lock cap is oriented facing the distal end of the stylet, the extensions of the drill stop of the stylet may be reversibly coupled with (inserted into) the slots of the luer lock on the proximal end of the cannula before, after, or during placement of the luer lock cap 413 over the proximal end of the stylet and sliding the cap to engage the distal end of the drill stop.

The diameters of the distal opening 476 and the internal threaded chamber 473 of the cap (including the internal threads 474) are sized such that they fit over the external diameter of the drill stop, and the external diameter of the proximal region of the luer-type lock (see, e.g., 237) to the extent that the diameters of the distal opening 476, the internal threaded chamber 473, and the internal threads 474 of the cap allow for threadable engagement between the internal threads of the cap and the projections of the proximal region of the luer lock (see, e.g., 234 and 237). Further, as discussed and shown above, the diameters of the components of the device 100 (including at least the luer lock, drill stop, the luer lock cap, and their component(s)) may be shaped to maximize difference(s) in exterior diameter(s) of the components held within the luer lock cap internal threaded chamber 473, including held by the proximal end 477 of the cap chamber 473 and the external diameter of the stylet (and, accordingly, also the diameter of the proximal stylet opening 472) so that the diameter of the proximal stylet opening 472 may be as small as possible compared with the diameters of the luer-type lock cap internal threaded chamber 473, the diameter between the internal threads 474, and the external diameter of the drill stop. This may not necessarily be required; but, may provide for enhanced containment of the components within the internal threaded chamber 473 of the luer lock cap 413.

Once the luer-type lock cap 413 is threaded over the proximal region (see, e.g., 237) of the luer-type lock and is threadably engaged by its internal threads 474 with luer lock projections (see, e.g., 234), which extend generally perpendicularly from the proximal region of the luer-type lock, the reversible threaded engagement of the internal threads of the cap and the external projections of the luer lock reversibly hold together the coupled engagement of the drill stop (and stylet as its attached to the drill stop) and the luer lock (and cannula as its attached to the luer lock). Due in part to the shape and size of the coupling members (the projections of the drill stop and the slots of the luer lock) the stylet and cannula are reversibly coupled (and held that way by the threaded engagement of the cap with the luer lock) in a manner that readily imparts rotation of the stylet (only) about its axis to rotation of the cannula also about its axis (and vice versa). Therefore, and as discussed below, rotation of the stylet only causes rotation of both the stylet and the cannula.

For example, on may attach a power drill to the stylet only (for example, by engaging the proximal end of the stylet within a bit of a surgical drill) and use the power drill to turn the stylet about its axis. Because of the coupling of the stylet and cannula (via the drill stop, luer lock, and cap), power rotation of the stylet causes rotation of both the stylet and cannula. This, for example, provides for a ready and reversible ability to drive a cannula and a stylet concurrently by connecting a surgical power drill only to the stylet (or only to the cannula). The same holds true for manual rotation of the stylet or cannula.

Further, and as discussed below, the rotation of the stylet, or cannula and stylet linked together, may also be used in a reverse direction from that used, for example, to insert the device into a bone. Thus, one may also use a power source (or manual source) to rotate both the stylet and the cannula in reversing the device(s) from a bone. As with insertion, in reverse rotation, a power tool may be connected only to the stylet (or cannula) in order to rotate both concurrently when they are coupled as described herein.

While not be limitation, it is understood that the arrangement of the drill stop extensions fitting into the luer lock slots, both arranged and engageable in an axial direction, provides for maximum contact between the components for the force of rotation to be imparted from one component to another, such as from the stylet, via the drill stop extensions, to the cannula, via the slots and slot sides in the handle luer lock.

Figure 4A:
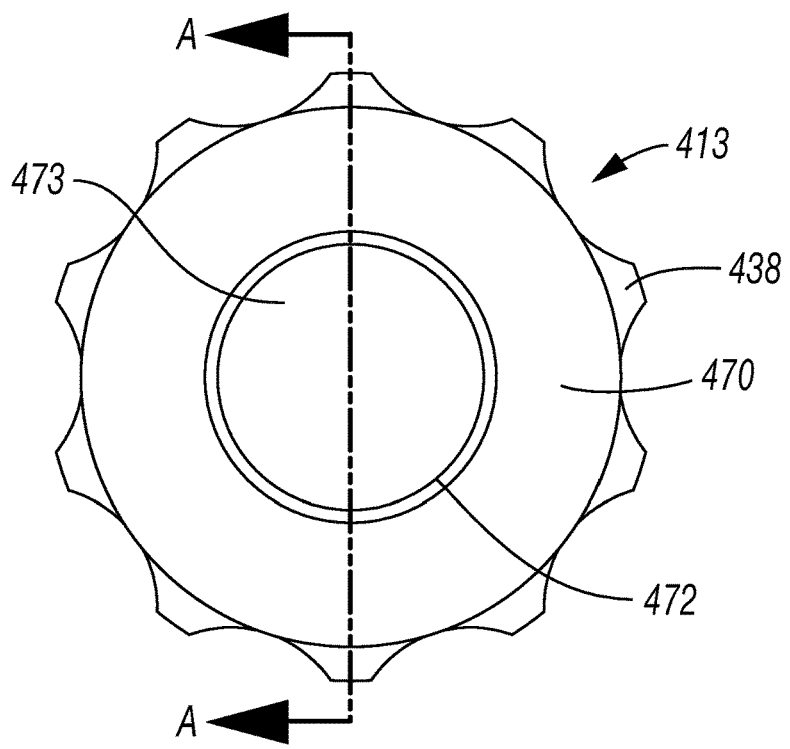
FIG. 4A shows an end view of the proximal end of the luer lock cap of FIG. 4. Also shown is the cross section line A-A, which forms the basis of the cross sectional view of FIG. 4B.

FIG. 4A shows a view of the external surface of the proximal end 470 of the luer lock cap 413, with cross section A-A indicated (the A-A cross section shown in FIG. 4B below). FIG. 4A also shows proximal stylet opening 472, internal threaded chamber 473, and external gripping feature 438.

Figure 4B:
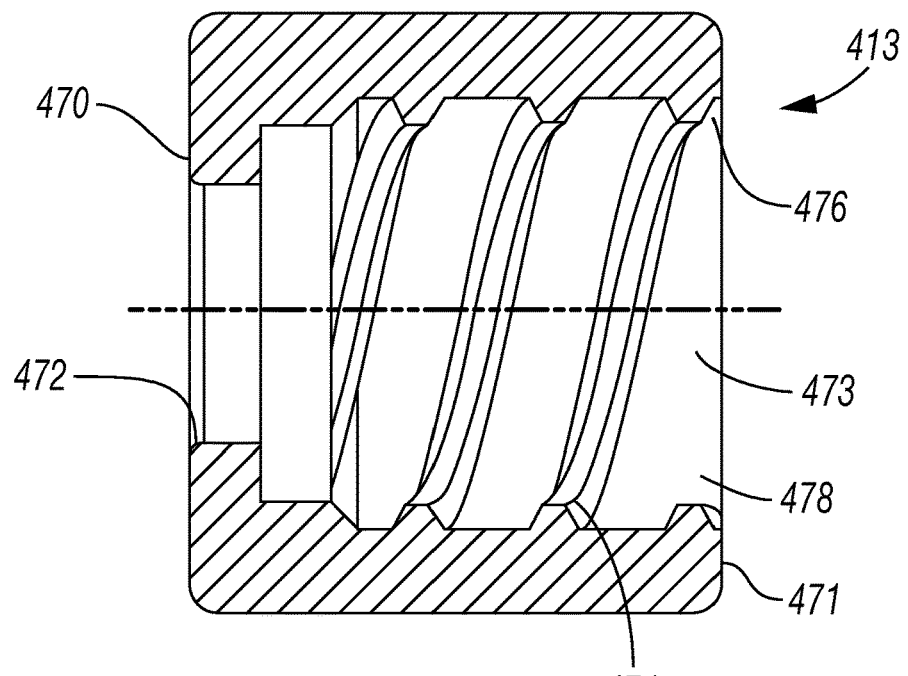
FIG. 4B is a cross sectional view of the luer lock cap of FIG. 4, along the cut A-A shown in FIG. 4A.

FIG. 4B is a cross section view along the cross section A-A shown in FIG. 4A. The figure shows the luer lock cap 413, with a distal end 471 and a proximal end 470. Proximal stylet opening 472 and distal opening 476 to internal threaded cavity 473 are also shown, as are internal thread(s) 474.

As discussed throughout, luer lock cap 413 reversibly couples a stylet or elongated wire (e.g., 104) with a cannula or elongated tube (e.g., 101) in, for example, device 100. For example, when a stylet 104 has a drill stop 312 firmly attached to a proximal region of the stylet (proximal to the proximal end of the stylet), and the stylet is inserted distal end first into a proximal opening 239 in the luer lock and into a channel or lumen 232 that passes through the interior of the luer lock, and the luer lock is attached to, at, or proximate the proximal end of a cannula, distal extensions 353 of the drill stop 312, extend distally from the drill stop (whether and wherein the distal extensions 353 may be considered to be a part of the drill stop 312 and/or component parts of drill stop 312). For example, a drill stop having two extensions located on opposing sides of the stylet (while noting that the invention includes different numbers of extensions) when attached to a stylet as described herein, the drill stops will extend along opposing sides of the drill stop (e.g., 112 and/or 312) and, therefore, the stylet 104. Thus, when the stylet is inserted into the proximal opening of the luer lock and is passed through the luer lock channel or lumen 232, the distal end of the stylet or elongated wire passes into and through the lumen of the cannula until the distal end of the drill stop meets the proximal end of the luer lock.

When the proximal end of the luer lock meets the distal end of the drill stop, the drill stop extensions 353 snugly and firmly, but reversibly, slidably engage with luer lock slots 235, having slot walls 236, the slots oriented toward and opening to the proximal end of the luer lock. The slots and the extensions are sized such that when the extensions and slots are aligned, the extensions of the drill stop are reversibly insertable into the slots of the luer lock.

As discussed herein and as shown in the figures, the lengths (from proximal to distal) of the extensions and slots (and/or the widths) are such that contact between the two is stabilized or even enhanced especially in a direction perpendicular to the axis of the device 100. This arrangement is believed (but not by limitation) to be effective or especially effective in transferring, for example, rotational force about the axis (i.e., perpendicular to the axis) of the stylet to the cannula, allowing rotational force applied about the axis of the stylet only to cause (but not by limitation substantially concurrently) rotation in the same direction about the cannula as well (and vice versa; i.e., rotation about the axis of the cannula alone causes rotation about the axis of the coupled stylet).

Luer lock cap 413 secures this coupling of the luer lock—cannula and drill stop—stylet by, for example, and prevents the extensions of the drill stop on the stylet from unintentionally becoming uncoupled (including but not limited to fully uncoupled or partially uncoupled, such as a partial insertion of the drill stop extensions into the luer lock slots).

Luer cap 413 assures reversible coupling by threadedly holding together the drill stop on the stylet and the luer lock at the proximal end of the cannula. As discussed throughout, this may be achieved by cap 413 having an internal threaded chamber 473, with internal thread(s) 474, with an opening 476 to the chamber at the cap's distal end 471 and a stylet opening 472 to the chamber at the cap's proximal end 470, wherein the diameter of the stylet opening 472 is less than the diameter of the distal opening 476; the internal diameter (including between the internal threads 474) of the distal opening 476 and of the inner threaded chamber 473 is greater than the outer diameter of the drill stop 312 and of the external diameter of the proximal region 237 of the luer lock 207; and the diameter of the stylet opening 472 is less than outer diameter of the drill stop 312 and of the external diameter of the proximal region 237 of the luer lock 207.

In this arrangement, luer lock cap 413 is applied over the proximal end of a stylet having a drill stop attached thereto distal to the proximal end of the stylet, the cap being slid over the proximal end of the stylet with the distal end 471 of the cap leading. When the distal end of the cap meets the proximal end of the drill stop fixed to the stylet, the entire drill stop, including the drill stop extensions (e.g., 353) (and the stylet), enters the internal threaded chamber 473 of the luer lock cap 413. However, the drill stop does not extend beyond the proximal wall 477 of the internal chamber of the luer lock cap. The drill stop is held within the luer lock cap 413 because the diameter of the stylet opening 472 in the proximal end 477 of the cap is too small to allow passage of the larger outer diameter of the drill stop (or as discussed below, the outer diameter of the proximal end 230 of the luer lock 207. Hence, the drill stop is held by the wall 477 at the proximal end of the internal threaded chamber 473, while the portion of the stylet proximal from the drill stop—cap extends through the stylet opening 472 to the proximal end 106 of the stylet 104.

Further, whether the drill stop projections have already been engaged with the slots of the luer lock attached at the distal end of the cannula, or even if the stylet has or has not been inserted into the cannula, in any event, the stylet is fully inserted into the cannula (into at least one lumen on the cannula) having attached at its proximal end a handle luer lock (e.g., 207). For example, the stylet may be partially inserted into the cannula when the cap is added, then fully assembled, then the cap threadably coupling the coupled drill stop—styled and luer lock—cannula. Another non-limiting example is for the stylet—drill stop to be fully engaged with the luer lock—cannula (i.e., with the drill stop extensions fully engaged in the luer lock slots) before adding the luer lock cap and coupling the device with the cap. Further, the cap may be added to the proximal end, and even moved to engage the drill stop, before the stylet is inserted into the cannula.

When the drill stop extensions—stylet and the luer lock slots—cannula are fully engaged, the proximal opening and the internally threaded chamber of the luer lock cap are slid over both the exterior of the drill stop and the proximal region of the luer lock, including over the outer diameter of the luer lock projections.

The luer lock reversibly threadably holds together the coupled stylet and cannula by receiving the drill stop within its internal threaded chamber 473 and further by receiving a proximal region of the luer lock (e.g., 237). As with the drill stop, the outer diameter of the proximal region of the luer lock (including of the projections 234) is less than the internal diameter of the internal threaded chamber 473 and the opening to the chamber 476. Therefore, the cap 413 fits over the proximal region of the luer lock (e.g., 237) including over the luer lock projections (e.g., 234). The cap is then reversibly threaded (for example but not by limitation, in a clockwise direction) onto the luer lock by an interaction of the internal threads 474 and the luer lock projections (e.g., 237). There is sufficient room between the location of the luer lock projections (generally at or close to the proximal end of the luer lock) and the remaining portion of the luer lock proximal region so that the cap may readily be threaded over the projections to a desired tightness without being obstructed by running against wider portions of the luer lock distal to luer lock proximal region 437 (such as the luer lock handle (see, e.g., FIG. 2)). However, the device 100 is also designed so that when a luer lock cap is fully threadably engaged with the luer lock projections, the distal end of the luer lock cap substantially threads up against (near to or flush with) the proximal end of the handle luer lock 207.

In use, and by non-limiting example, an elongated wire or stylet having a drill stop, as disclosed herein, permanently attached to it, as described herein, is inserted into an elongated tube or cannula, having a lumen sized to slidably receive the stylet. The cannula has attached at, to, or proximate its proximal end a luer lock, as disclosed herein.

The stylet is slid into the proximal opening of the luer lock and subsequently into the lumen of the cannula. When the drill stop of the stylet meets the proximal end of the luer lock, extensions on the drill stop fit snugly but reversibly into corresponding slots in the luer lock as described herein.

A luer lock cap having a distal end facing the drill stop and luer lock is slid over the proximal end of the stylet, with the distal end of the cap facing the drill stop and luer lock. The cap is slidable along the drill stop through a stylet opening at the axial end of the luer lock cap. Once the luer lock cap is slid to the proximal end of the drill stop, the distal opening and an internally threaded chamber of the cap fit over and receive the drill stop. Because the diameters of the distal opening and internally threaded chamber are larger than the external diameter of the drill stop, but the diameter of the stylet opening at the proximal end of the cap is smaller, the luer lock cap fully slides over the drill stop, and is held in place within the internally threaded chamber of the cap as the smaller diameter of the stylet opening at the proximal end of the cap chamber will not allow the drill stop to exit the proximal end of the cap. Thus, the luer lock cap holds the coupled stylet and cannula together by reversibly holding the drill stop (with extensions) against the luer lock (with slots).

As discussed above, the location of placement of the drill stop on the stylet determines the length of elongated wire that will extend into and through the cannula. For example, in some embodiments it may be desirable to have a small amount of, for example a sharp tipped stylet extend beyond the distal end of the distal end of the cannula. This may, for example, allow for more precision in targeting drilling by, for example, allowing the sharp tipped cannula to form an initial hold hole in the exterior of bone at a location desired to be accessed. This may help avoid, for example, problematic skidding of the device 100 along the surface of bone when initiating drilling (and may also, for example, allow for more precisely directed drilling within bone).

In embodiments of the invention, a power surgical drill, wire driver, or similar power drill is engageable with the proximal end 106 of the elongated wire or stylet 104. For non-limiting example, the proximal end of the stylet may fit into a chuck of a surgical drill similarly to how a proximal end of a typical drill bit (the proximal end being opposite the distal, drilling end) reversibly engages with the chuck of a typical power drill. For example, the proximal end 106 of the stylet 104 may be reversibly insertable into a drill chuck (not shown) of a surgical drill (not shown) and held firmly but reversibly therein by reversible tightening of dogs of the chuck, tightened for example by a chuck key (not shown). In such embodiments, rotation of the surgical power tool chuck causes rotation about the axis of the engaged stylet. As discussed above, because of the reversible coupling of the stylet to the cannula, rotation of the coupled stylet causes rotation about the axis of the coupled cannula as well.

In embodiments of the invention, the drill may be attached to the stylet at any time or times within the use of the device. For example, it may be attached to the proximal end of a stylet that has attached thereto a drill stop before, during, or after coupling of the stylet and the cannula.

In non-limiting embodiments of the invention, the device is used to inject an injectable matter, such as bone graft substitute, into an intraosseous lesion for treatment of the lesion. In doing so, a drill stop is permanently affixed to a stylet, such as by welding a stainless steel drill stop to a stainless steel stylet, at a desired location. Others ways of firmly or permanently (at least well over the lifetime of the instrument) affixing the drill stop to the stylet are also within the scope of the invention, such as but not limited to adhesives including epoxy, or mechanical interference connection such as a press fit spline.

As discussed above, for example, the drill stop may be located at a position that will place a desired amount of the distal end of the stylet in a cannula. For example, a drill stop may be placed such that the distal length of the wire extends beyond the distal end of a cannula containing the wire; this may be especially applicable, but not limited to, devices in which the stylet has a sharp or pointed distal tip. The stylet may also be obtained with the drill stop already attached. For example, in embodiments, a stylet may be formed with a drill stop as an integral part of the same body. In other embodiments, a stylet having a drill stop already attached at a desired location may be used by a medical professional in assembling the device.

In embodiments of the invention, the material(s) making up the components are not limited other than by biocompatibility. For example, the cannula, and/or stylet, and/or luer lock, and/or luer lock cap may be made of stainless steel, polymers (e.g., medically acceptable polymers), other metal(s), and any mixtures thereof. Also, while the cannula and the stylet are generally not flexible, in embodiments of the invention, one or both may be semi-flexible.

Also provided is a cannula having a luer lock permanently attached at, to, or proximate its proximal end. For example, a stainless steel luer lock may be welded to a stainless steel cannula. Others ways of firmly or permanently (at least well over the lifetime of the instrument) affixing the luer lock to the cannula are also within the scope of the invention, such as but not limited to adhesives.

The invention further discloses that the slots of the luer locks (both of the handle luer lock and the simple luer lock) are not in commercially available luer locks, but are added to them (e.g., cut into them) as a part of this invention.

The luer lock may be provided separately from the cannula and attached to the cannula prior to assembly of the device. In other embodiments, the cannula may be provided with the luer lock already affixed thereto.

In embodiments of the invention, a cannula having a luer lock affixed at its proximal end and a stylet having a drill stop affixed at a desired location are reversibly coupled as described above. Briefly, the distal end of a stylet is inserted into the proximal end of the luer lock, which is located at the proximal end of a cannula. The stylet is then slid into a lumen in the cannula which slidably receives the stylet until the extensions of the drill stop (discussed above) are aligned and inserted into the slots in the proximal end of the luer lock (as discussed above). This results in a snug but reversible coupling between the luer lock—cannula and the drill stop—stylet.

As described above in detail, in embodiments of the invention a luer lock cap having a distal opening, an internal threaded chamber, and a proximal stylet opening is slid over the proximal end of the stylet and slid, with the cap's distal end facing the drill stop and luer lock, distally down the stylet until it meets the proximal end of the drill stop.

The entire drill stop then enters the interiorly threaded chamber of the luer lock cap until it is held in place by the proximal wall of the luer lock, while the proximal portion of the stylet exits the proximal end of the cap through a stylet opening that fits the diameter of the stylet but is smaller than the exterior diameter of the drill stop.

The proximal end of the coupled luer lock also enters the distal opening of the luer lock cap. Projections of the luer lock, extending perpendicularly or radially, or substantially perpendicularly or radially to the axis of the device into the internally threaded chamber of the cap then threadably engage the internal threads of the internally threaded chamber of the luer lock cap. The luer lock cap is then twisted (e.g., clockwise) until the cap has been snugly but reversibly threadably engaged with the luer lock. At this point, the stylet and the cannula are reversibly coupled both by the insertion of the drill stop extensions on the stylet into the slots in the luer lock of the cannula and by the luer lock cap reversibly threadably holding the distal end of the drill stop (and thus the extensions) against the proximal end (and thus the slots) of the luer lock.

In this fully assembled form, a power drill, such as a surgical wire drill, may be engaged with the proximal end of the stylet (and/or or to a region of the stylet located between the proximal end of the cap and the proximal end of the stylet). For example, as discussed above, the distal end of the stylet may be reversibly engaged with a chuck of a drill, similarly to how a typical drill bit is engaged with a chuck of a drill.

The device is then positioned on a desired location on the surface of a bone where a medical professional desires to drill to reach a bone region to be treated, such as a bone marrow lesion within a specific intraosseous space. In non-limiting embodiments of the invention, the location may be on the surface of a bone above a BML to be treated, such as above a BML in the knee, including intraosseous spaces in the medial and lateral femoral condyle and medial and lateral tibial plateau near the subchondral plate.

However, BML are not unique to the knee; BML have been found in at least, but not limited to, bones in ankle, foot, hand, shoulder, and hip. Therefore, devices of embodiments of the invention may be used in other bones with BML, including but not limited to, bones in ankle, foot, hand, shoulder, and hip, where BML have also been found.

Embodiments of the invention may also be used for accessing interior regions of bones for any purposes, including for example, for injecting (and optionally first withdrawing) agents to (or from) a site within a bone wherein the site might not technically qualify as a BML but a surgeon has some reason for desiring to access (and to inject into (or withdrawal from) the site).

In embodiments, prior to reaching the bone surface, the device may be used to drill through tissues above the bone surface in order to reach the desired bone surface. When at a desired location on a bone surface, the distal end of the device is positioned against the bone and the drill activated to axially rotate the stylet and cannula to drill into the bone to a desired depth and location (generally, but not necessarily, to the location of a bone marrow lesion to be treated). As discussed above, in embodiments of the invention, the stylet may be pointed and extend beyond the distal end of the cannula. In such embodiments, the pointed distal end may establish an initial insertion point or hole in order to help keep the device from skidding from the desired point on the device and/or to aid in further insertion of the device into bone.

When the desired location within the bone is reached (which in embodiments of the invention may be determined at least in part by depth markers on the exterior of the cannula), the rotation is stopped, the cannula is kept in place, and the stylet is reversibly uncoupled from and removed from the cannula. For example, in embodiments, once the device has reached a desired location in bone, the luer lock cap is twisted (threaded) off the projections of the luer lock and removed from at least the luer lock. This allows a medical professional to pull (generally, gently) the stylet from the cannula, specifically, to pull the extensions of the drill stop from the slots of the luer lock. When the cannula has been fully uncoupled from the stylet, the stylet is drawn from the lumen of the cannula and from the luer lock. At this point, the cannula (and luer lock), only, remain inserted in the bone, and in the original desired location. The stylet may be placed in a sterile environment.

A source of bone marrow treatment substance, such as a syringe (not shown), having a standard luer lock connection is then reversibly engaged with the luer lock on the end of the lumen. For example, in embodiments of the invention, the luer lock on the source of the bone marrow treatment substance is a positive mating feature ("male") luer lock connection that reversibly engages with the negative mating feature luer lock projections ("female") (for example, by reversibly twisting the female luer lock connection into threads in the sleeve of the male connection).

A bone marrow treatment substance, such as bone graft substitute, is then injected into the cannula from the injection device (e.g., a syringe) that is engaged with the proximal end of the cannula. The treatment substance flows through the lumen of the cannula, exits the distal opening of the cannula and enters the desired region of the bone to be treated.

Following satisfactory injection of bone treatment substance, the cannula may be pulled and/or twisted manually from the bone by a medical professional, or the device may be reassembled and a power drill used to rotate the device in the direction opposite the drilling rotation to reverse the cannula and stylet out of the bone.

For example, after injection into the bone of the treatment substance, and after uncoupling of the source of bone treatment substance from the luer lock of the proximal end of the cannula, the stylet is then reinserted into the luer lock and subsequently into the lumen of the cannula until the extensions of the distal end of the drill stop on the stylet reversibly engage with the slots in the distal end of the luer lock at the proximal end of the cannula—reversibly recoupling the stylet and the cannula. The luer lock cap is then added back to the proximal end of the stylet, slid to receive the drill stop within its internally threaded chamber, and snugly but reversibly threaded over the projections of the lumen, thus fully recoupling the stylet with the cannula. The proximal end of the stylet may then be engaged again with a power drill as discussed above, and the stylet rotated in the direction opposite the direction used to insert the device into the bone. This counter rotation helps remove the device from the bone.

Reinserting the stylet into the cannula will also help clear any remaining substance out of the device, if any, and push it into the intraosseous space. Further, because the device is fully reversibly coupleable multiple times, embodiments of the device may be assembled, used on a patient, disassembled, cleaned and sterilized and used again on the same or a different patient. However, it is also within the scope of the invention that the device be for single use only.

The handle 208 (and/or 108) of the handle luer lock 207 is a component, integral part of the luer lock. Therefore, when the luer lock 207 is attached to the cannula 101 the handle 208 does not move (twist or rotate) relative to the cannula 101. Functions, purposes, or uses of the handle are, for non-limiting examples, to allow a person to grip or hold the cannula firmly and precisely when, for example, assembling (coupling), drilling with, disassembling (decoupling), and reassembling (recoupling) the device 100. This may be further assisted by the external handle gripping feature 238. For non-limiting example, when threading the luer lock cap 413 to the luer lock 207, one may grip both the handle 208 of the luer lock 207 and the external gripping feature of the 438 of the luer lock cap 413. The handle 208 may also be used, for example, to assist in attaching the luer lock to the proximal end of a cannula and to assist in handling the cannula when the luer lock is attached, such as when inserting or removing a stylet from a cannula.

FIG. 5 is a perspective view of a partially assembled simple luer lock (luer-type lock) device 500 (shown fully assembled in FIG. 5A). Simple luer lock device 500 differs from handle luer lock device 100 of FIGS. 1-4B by at least not having the luer lock handle 208. Instead, the luer lock 580 is of the same or substantially the same exterior diameter throughout its length, except for the proximal end of the luer lock which has a region of increased external diameter corresponding to the external diameter of the luer lock projections 534, which extend perpendicularly, or substantially perpendicularly, to the axis of the luer lock, and the axis of the cannula when the luer lock is attached to the proximal end of the cannula (similar to the projections of the handle luer lock of device 100 (see, e.g., FIG. 2, 207 (handle luer lock), and 234 (projections of handle luer lock)).

FIG. 5 also shows, each similar to those described above for handle luer lock device 100: a stylet 504 having a proximal end 506 and a drill stop 512 with drill stop extensions 553 attached thereto; the stylet being partially inserted into a lumen (not shown) of a cannula 501 having a distal end 502 with optional teeth 511 about the distal end of the cannula; with the cannula having attached to, at, or proximate its proximal end simple luer lock 580 (differing from the handle luer lock in at least not having a handle, as shown herein) having luer lock projections 534; and luer lock cap 513 with distal end 515 and proximal end 514.

FIG. 5A shows a perspective view of assembled simple luer lock (luer-type lock) device 500 (shown partially assembled in FIG. 5). FIG. 5A shows, each similar to those described above for handle luer lock device 100, a stylet 504 having a proximal end 506 and a pointed and/or sharpened distal end 505, extending beyond the distal end 502 of the cannula 501, and depth markers 510 on cannula 501. Also shown in FIG. 5A is luer-type lock cap 513 with distal end 515 and proximal end 514. A distal section of simple luer lock 580, extending beyond cap 513 is also shown.

FIG. 5B shows a perspective view of simple luer lock 580, having a proximal end 531, a distal end 530, a channel 532 extending axially through simple luer lock 280, a distal opening 540 to chamber 532 at the distal end 530 of simple luer lock 580, and a proximal opening 539 to chamber 532 at the proximal end 531 of simple luer lock 580.

Also shown in FIG. 5B are two (yet, some embodiments of the invention may contain one, or more than two) luer lock projections 534 at the proximal end 531 that extend perpendicularly or radially, or substantially perpendicularly or radially from the axis of the simple luer lock 580.

FIG. 5B further shows a channel 532 that opens to both the distal end 230 and the proximal end 231 of simple luer lock 580. The channel 532 extends axially through the luer lock 580, between the openings at the proximal and distal ends of the luer lock. As shown below, the channel 532 is substantially cylindrical, yet the internal diameter of the chamber may change within the luer lock. FIG. 5B shows the proximal opening 539 of channel 532.

Additionally, FIG. 5B shows slots 535, having sides 536, extending linearly, or substantially linearly, with the axis of the luer lock into the wall 582 of the luer lock 580.

The functions and structures of the simple luer lock 580, including the projections 534 and the slots 535, are similar to those shown above for the handle luer lock 207. For example, the luer lock 580 is permanently (at least over the lifetime of the device) attached at the proximal end of cannula 501, with the lock snugly inserted into the, or a, lumen of the cannula up to a point to where the luer lock projections 534 remain outside the cannula. The luer-type lock couples a cannula and a stylet, having a drill stop 512 permanently (at least over the lifetime of the device) attached thereto, by snugly but reversibly receiving extensions 553 from the distal end of drill stop 512, which extend linearly or substantially linearly along the axis of the stylet and are sized to reversibly and snugly engage within the luer lock slots 535 of the luer lock 580. When the extensions 553 of the drill stop 512 are fully or substantially fully inserted into the slots 535 of the luer lock 580, rotation about the axis of the stylet causes similar rotation about the axis of the cannula (and vice versa).

While not required for embodiments of the disclosed invention (including for handle luer lock embodiments), the reversible coupling of the cannula and the stylet may be further enhanced and/or stabilized (e.g., but not limited to, in withdrawing the reassembled device) by luer lock cap 513 (substantially as described above, by example, for luer lock cap 413) coupling the distal end of the drill stop to the proximal end of the luer lock, thereby coupling the drill stop extensions 553 within the luer lock slots 535, by threadably engaging the luer lock projections 534 with internal threads (see, e.g., 474) within the luer lock cap interior (see, e.g., luer lock cap internal threaded chamber 473). In this configuration too, rotation about the axis of the stylet, for example, by a power drill attached to the proximal end of the stylet, causes similar rotation about the axis of the cannula coupled to the stylet.

FIG. 5C is a side view of simple luer lock 580. Similar to FIG. 5, the simple luer lock is similar to the handle lure lock 207 as described above; however, simple luer lock 580 is different at least in not having a handle (e.g., in lacking a handle similar to that of handle 208). FIG. 5C shows distal end 530, proximal end 531, external surface 581, and distal opening 540 of simple luer lock 580. The figure further shows projections 534, slot 535, and slot sides 536. Still further, FIG. 5C shows the cross section line A-A, which extends axially through the luer lock 280, and which forms the basis of the cross sectional view of FIG. 5D.

FIG. 5D is a cross sectional view along the cut A-A shown in FIG. 5C. FIG. 5D shows the simple lure lock 580 having distal end 530, proximal end 531, distal end opening 540, a proximal opening 539, and external surface 581. FIG. 5C also shows that in embodiment depicted, the interior diameter of the channel 532 is smaller toward the distal end of the luer lock 580 than toward the proximal end. However, and as discussed above for handle luer lock 207, the diameter of the channel toward the distal end must allow the external diameter of a cannula (e.g., of cannula 501, including at its proximal end) to fit securely within the channel, or in other embodiments, to fit securely over the external diameter of the simple luer lock 580 up to the positions where the projections 534 remain outside the lumen of the luer-type lock. The diameter of the channel throughout the simple luer-type lock must allow the external diameter of a stylet (e.g., stylet 504 of FIG. 5) to reversibly pass through the channel 532 (and reversibly into a lumen of the cannula 501).

FIG. 5E is an end view, looking toward the distal end 530 of simple luer lock 580. FIG. 5E shows the distal opening 540 of the channel 532, and the simple luer lock projections 534.

FIG. 5E also shows the cross section line B-B, which forms the basis of the cross sectional view of FIG. 5F.

FIG. 5F is a cross sectional view along the cut B-B shown in FIG. 5E. FIG. 5F shows the distal end 530, proximal end 531, and channel 532 which passes axially through the luer lock 580, between proximal opening 539 and distal opening 540. In the embodiment shown in FIG. 5E, the internal diameter of the channel 532 at the proximal end 531 of the luer lock 580 is larger than the external diameter of the cannula 501. Therefore, in order for cannula 501 to fit snugly into the channel 532 of luer lock 580 at distal end 530 of luer-type lock 580, the internal diameter of channel 523 at the distal end 530 of the luer lock 580 is less than the internal diameter of the channel 523 at the proximal end 531 of the luer lock 580; the internal diameter of the channel 523 at the distal end 530 of the luer lock 580 thereby being sized to snugly receive the external diameter of the cannula 501. While not by limitation, it is believed that this aspect of the luer lock helps make strong and a fluid tight attachment between the cannula and the luer lock, thereby, for example, preventing substances from leaking out of the device as they flow through.

Further, for example for other embodiments related to FIGS. 5-5F, the external diameter of the luer lock 580—except for that of the projections 534—must be small enough for the internal diameter of the lumen of the cannula to securely receive and to fit over the exterior of luer-type lock 580 but for the external diameter of the projections 534, and the internal diameter of the entire length of channel 532 must allow the external diameter of a stylet 504 to slidably pass through the channel.

FIG. 5F also shows an outward taper 541 in the interior diameter of the channel 532. This taper allows, for example, increased ease in engaging the outer diameter of the distal end of the elongated wire or stylet 504 (see, e.g., the distal end 103 of the 104) within the channel 532. Also shown in FIG. 5F is a chamfer 542 located proximate the proximal end 531 of the luer lock channel 532 proximal opening 539. This chamfer allows, for example, the diameter of the channel 532 to further increase beyond that of the taper 541 proximate the proximal opening of the channel 532. Like the taper 541, the chamfer 542 may assist in receiving the distal end (see, e.g., 105) of the stylet 504 into the proximal opening 539 of channel 532.

What is claimed is:

1. A medical device for accessing intraosseous space comprising:
    an elongated tubular member having a proximal end and a distal end, at least one lumen extending therethrough, and a luer-type lock at the proximal end;
    the luer-type lock comprising a tubular body having a distal and a proximal end, a channel therebetween, and at least two projections projecting radially from and/or near the proximal end of the tubular body;
    the luer-type lock further comprising at least two slots in the body, extending from the proximal end toward the distal end coaxially with the channel;
    an elongated wire slidably engageable within the at least one lumen of the elongated tubular member, having a proximal and a distal end, and a drill stop attachable thereto;
    the drill stop comprising a distal and a proximal end, and an opening having an axis extending therebetween through which a portion of the elongated wire is extendable therethrough and attachable to the drill stop therein; and
    the drill stop comprising at least two drill stop extensions extending distally from the distal end and coaxially with the axis of the opening, the drill stop extensions reversibly insertable within the slots of the luer-type lock.

2. The medical device of claim 1, further comprising a luer-type lock handle.

3. The medical device of claim 1, further comprising a cap comprising a proximal and a distal end, and an internal threaded chamber therebetween, the chamber opening to the distal end and reversibly receivable of the drill stop, and reversibly threadable with the projections of the luer-type lock; the cap capable reversibly holding the distal end of the drill stop against the proximal end of the luer-type lock, the extensions of the drill stop within the slots of the luer-type lock, and the elongated wire within the elongated tubular member.

4. The medical device of claim 3, wherein a drill is attachable to the proximal end and/or a proximal end region of the elongated wire.

5. The medical device of claim 4, wherein the drill is a power drill.

6. The medical device of claim 5, wherein the drill is capable of rotating the elongated wire about the axis of the wire causing synchronized rotation of the elongated tubular member when the wire and the member are reversibly engaged by reversible insertion of the drill stop extensions into the luer-type lock slots and reversible threading of the cap with the luer-type lock projections.

7. The medical device of claim 4, wherein the drill is capable of rotating the elongated wire about the axis of the wire causing synchronized rotation of the elongated tubular member when the wire and the member are reversibly engaged by reversible insertion of the drill stop extensions into the luer-type lock slots and reversible threading of the cap with the luer-type lock projections.

8. The medical device of claim 1, further comprising the drill stop attachable or attached to a location on the elongated wire to allow a desired amount of wire distal the drill stop to slidably enter the proximal end of the luer lock and the elongated tubular member.

9. The medical device of claim 8, wherein the desired amount of wire distal the drill stop to slidably enter the proximal end of the luer lock and the elongated tubular member is sufficient to allow the wire to extend distally beyond the distal end of the elongated tubular member.

10. The medical device of claim 1, wherein a drill is attachable to the proximal end and/or a proximal end region of the elongated wire.

11. The medical device of claim 10, wherein the drill is a power drill.

12. The medical device of claim 11, wherein the drill is capable of rotating the elongated wire about the axis of the wire causing synchronized rotation of the elongated tubular member when the wire and the member are reversibly engaged by reversible insertion of the drill stop extensions into the luer-type lock slots.

13. The medical device of claim 10, wherein the drill is capable of rotating the elongated wire about the axis of the wire causing synchronized rotation of the elongated tubular member when the wire and the member are reversibly engaged by reversible insertion of the drill stop extensions into the luer-type lock slots.

14. A medical instrument for accessing intraosseous space comprising:
    cannula having a proximal and a distal end, and at least one lumen extending therebetween;
    a luer-type lock comprising a proximal and a distal end, a channel having an axis extending therebetween, the channel permanently attachable to the proximal end of the cannula;
    the luer-type lock further comprising a wall comprising a proximal and a distal end around the channel extending between the proximal and distal ends of the luer-type lock, and comprising at least two slots therein extending from the proximal end of the wall toward the distal end of the wall and coaxially with the axis of the channel;
    the luer-type lock further comprising at least two luer-type lock projections projecting radially at or near the proximal end of the wall;
    a stylet having a proximal and a distal end, the stylet slidably engageable within the at least one lumen of the cannula;
    a drill stop comprising a distal and a proximal end, and an opening having an axis therebetween, the drill stop opening slidable over the elongated wire, and permanently attachable to the elongated wire; and the drill stop further comprising at least two drill stop extensions extending distally from the distal end of the drill stop and coaxially with the drill stop opening, the drill stop extensions reversibly insertable within the slots of the luer-type lock when the distal end of the drill stop is proximate the proximal end of the luer lock.

15. The medical instrument of claim 14, further comprising a luer-type lock handle.

16. The medical instrument of claim 14, further comprising a cap comprising a proximal and a distal end, and an internal threaded chamber therebetween, the chamber opening to the distal end, reversibly receivable of the drill stop, and reversibly threadable with the projections of the luer-type lock; the cap capable reversibly holding the distal end of the drill stop against the proximal end of the luer-type lock, the extensions of the drill stop within the slots of the luer-type lock, and the stylet within the cannula.

17. The medical instrument of claim 16, wherein a drill is attachable to the proximal end and/or a proximal end region of the stylet and the drill is capable of rotating the stylet about the axis of the stylet causing synchronized rotation of the cannula when the stylet and the cannula are reversibly engaged by reversible insertion of the drill stop extensions into the luer-type lock slots and reversible threading of the cap with the luer-type lock projections.

18. A medical instrument kit having component parts capable of being assembled into a medical instrument, the kit comprising the combination of:
one cannula having an axis, a proximal end, and a modified luer lock at its proximal end;
the modified luer lock having a distal end attached thereat to the cannula, the modified luer lock further and comprising at least one side slot extending axially with the cannula in the side of the modified luer lock in the direction of the proximal end of the cannula;
one stylet having an axis and a drill stop attached thereto; and
the drill stop comprising a distal end and therefrom extending radially with the stylet at least one extension shaped to mate within the at least one slot in the modified luer lock.

19. The medical instrument kit of claim 18, further comprising:
the modified luer lock on the proximal end of the cannula having at its distal end at least two projections that project perpendicularly from the axis of the lumen;
one luer lock cap having a distal and a proximal end, the distal end having an opening to an internally threaded chamber, and the luer lock cap slidably engageable over the stylet;
the luer lock cap threadably engageable with the at least two projections of the modified luer lock through the opening and the internally threaded chamber of the luer cap threading over the at least two projections of the modified luer lock.

20. The medical kit of claim 18, further comprising:
1-3 negative mating luer-to-luer connectors.

21. The medical kit of claim 18, further comprising:
1-3 3 ml syringes.

* * * * *